US010940168B2

(12) United States Patent
Lee et al.

(10) Patent No.: US 10,940,168 B2
(45) Date of Patent: Mar. 9, 2021

(54) METHOD OF TREATING BRUCH'S MEMBRANE HYPOFUNCTION DISEASE

(71) Applicant: ALTREGEN CO., LTD., Yongin-si (KR)

(72) Inventors: Yunhee Lee, Jeonju-si (KR); Ali Hussain, London (GB); Dae Bong Kim, Seoul (KR)

(73) Assignee: ALTREGEN CO., LTD., Yongin-si (KR)

( * ) Notice: Subject to any disclaimer, the term of this patent is extended or adjusted under 35 U.S.C. 154(b) by 0 days.

(21) Appl. No.: 16/484,570

(22) PCT Filed: Feb. 8, 2018

(86) PCT No.: PCT/KR2018/001722
§ 371 (c)(1),
(2) Date: Aug. 8, 2019

(87) PCT Pub. No.: WO2018/147663
PCT Pub. Date: Aug. 16, 2018

(65) Prior Publication Data
US 2020/0023016 A1  Jan. 23, 2020

(30) Foreign Application Priority Data

Feb. 9, 2017  (KR) .................. 10-2017-0018196
Feb. 8, 2018  (KR) .................. 10-2018-0015887

(51) Int. Cl.
*A61K 35/616* (2015.01)
*A61P 27/02* (2006.01)
*A61K 9/00* (2006.01)
*A61K 36/258* (2006.01)

(52) U.S. Cl.
CPC .......... *A61K 35/616* (2013.01); *A61K 9/0048* (2013.01); *A61K 36/258* (2013.01); *A61P 27/02* (2018.01)

(58) Field of Classification Search
None
See application file for complete search history.

(56) References Cited

U.S. PATENT DOCUMENTS

| 6,767,890 | B1 * | 7/2004 | Collin | C07K 7/06 514/12.2 |
| 2006/0134226 | A1 * | 6/2006 | Leonard | A61K 33/30 424/638 |
| 2012/0309710 | A1 * | 12/2012 | Jiao | A61P 7/02 514/54 |
| 2014/0328951 | A1 * | 11/2014 | Shim | A61K 31/704 424/728 |
| 2019/0321381 | A1 * | 10/2019 | Lee | A23L 33/10 |

FOREIGN PATENT DOCUMENTS

| KR | 10-2006-0126876 A | 12/2006 |
| KR | 10-2009-0123195 A | 12/2009 |
| KR | 10-2011-0085026 A | 7/2011 |
| KR | 2014 017839 | * 2/2014 |
| KR | 10-2014-0045260 A | 4/2014 |
| KR | 10-2014-0045261 A | 4/2014 |
| WO | 00/29009 A1 | 5/2000 |

OTHER PUBLICATIONS

Lee et al., "Modulating the Transport Characteristics of Bruch's Membrane with Steroidal Glycosides and Its Relevance to Age-related Macular Degeneration (AMD)", Investigative Ophthalmology and Visual Science, vol. 56, No. 13 (Dec. 2015).
Hosokawa et al., "Bio-functions of Marine Carotenoids", Food Science and Biotechnology, vol. 18, No. 1 (2009).
International Search Report of corresponding Patent Application No. PCT/KR2018/001722—6 pages (dated Jun. 14, 2018).
Birkedal-Hansen et al., "Matrix Metalloproteinases: A Review", Critical Reviews in Oral Biology and Medicine, vol. 4, No. 2—54 pages (1993).
Bok, "Retinal Photoreceptor-Pigment Epithelium Interactions", Investigative Opthalmology & Visual Science , vol. 26—36 pages (Dec. 1985).
Bui et al., "The Contribution of Glycolytic and Oxidative Pathways to Retinal Photoreceptor Function", IOVS, vol. 44, No. 6—8 pages (Jun. 2003).
Chihara et al, "Resorption of subretinal fluid by transepithelial flow of the retinal pgment epithelium", Graefe's Archive for Clinical and Experimental Ophthalmology, vol. 223—3 pages (1985).
Emi et al., "Hydrostatic Pressure of the Suprachoroidal Space", Investigative Ophthalmology & Visual Science, vol. 30, No. 2—6 pages (Feb. 1989).
Esterbauer et al., "Chemistry and Biochemistry of 4-Hydroxynonenal, Malonaldehyde and Related Aldehydes", Free Radical Biology & Medicine, vol. 11—48 pages (1991).
Frambach et al., "The rate and route of fluid resorption from the subretinals pace of the rabbit", Ivest. Ophthalmol. Vis. Sci., vol. 22, No. 3—11 pages (Mar. 1982).

(Continued)

*Primary Examiner* — Ralph J Gitomer
(74) *Attorney, Agent, or Firm* — Knobbe Martens Olson & Bear LLP

(57) ABSTRACT

A composition includes a sea cucumber and ginseng/red ginseng composite extract which has the effect of regenerating the Bruch's membrane of the eye and improving the transport function of the Bruch's membrane. The composite composition improves the transport function of the Bruch's membrane and eliminates lipids accumulated on the membrane to promote the regeneration of the Bruch's membrane, thereby showing the effect of delaying or reversing the senescence process of the eye. Further, the composition is highly preventive or therapeutic of various diseases attributed to a decrease in the function of the Bruch's membrane with age, including age-related macular degeneration (AMD) and can solve the problem associated with the eye health maintenance of ordinary persons and with the transport reduction, resulting from senescence, of vitamins, metals, and anti-oxidative materials.

10 Claims, 14 Drawing Sheets

(56) References Cited

OTHER PUBLICATIONS

Guo et al., "Age-Dependent Variation in Metalloproteinase Activity of Isolated Huan Bruch's Membrane and Choroid", Investigative Opthalmology & Visual Science, vol. 40, No. 11—7 pages (Oct. 1999).
Handa et al., "Increase in the Advanced Glycation End Product Pentosidine in Bruch's Membrane with Age", Investigative Ophthalmology & Visual Science, vol. 40, No. 3—5 pages (Mar. 1999).
Holz et al., "Analysis of Lipid Deposits Extracted From Human Macular and Peripheral Bruch's Membrane", Arch. Ophthalmol., vol. 112—5 pages (Mar. 1994).
Hughes et al., "Effects of Cyclic AMP on Fluid Absorption and Ion Transport Across Frog Retinal Pigment Epithelium", The Journal of General Physiology, vol. 83—25 pages (Jun. 1, 1984).
Hussain et al., "Age-related alterations in the diffusional transport of amino acids across the human Bruch's-choroid complex", Journal of the Optical Society of America, vol. 19, No. 1—7 pages (Jan. 2002).
Hussain et al., "Transport Characteristics of Ageing Human Bruch's Membrane: Implications for Age-Related Macular Degeneration (AMD)", In: Focus on Macular Degeneration Research, Chapter IV—12 pages (2004).
Hussain et al., "Macromolecular diffusion characteristics of ageing human Bruch's membrane: Implications for age-related macular degeneration (AMD)", Experimental Eye Research, vol. 90—8 pages (2010).
Hussain et al., "High Molecular-Weight Gelatinase Species of Human Bruch's Membrane: Compositional Analyses and Age-Related Changes", Investigative Ophthalmology & Visual Science, vol. 51, No. 5—9 pages (May 2010).
Hussain et al., "Disturbed Matrix Metalloproteinase Activity of Bruch's Membrane in Age-Related Macular Degeneration", Investigative Ophthalmology & Visual Science, vol. 52, No. 7—8 pages (Jun. 2011).
Hussain et al., "Disturbed Matrix Metalloproteinase Pathway in Both Age-Related Macular Degeneration and Alzheimer's Disease", Journal of Neurodegenerative Diseases, vol. 2017—14 pages (Jan. 18, 2017).
Karwatowski et al., "Preparation of Bruch's membrane and analysis of the age-related changes in the structural collagens", British Journal of Ophthalmology, vol. 79—9 pages (Oct. 1, 1995).
Kassof et al., "A Randomized, Placebo-Controlled, Clinical Trial of High-Dose Supplementation with Vitamins C and E, Beta Carotene, and Zinc for Age-Related Macular Degeration and Vision Loss: AREDS repot No. 8", Arch Ophthalmol., vol. 119, No. 10—44 pages (Oct. 2001).
Kumar et al., "Increased Sequestration of Matrix Metalloproteinases in Ageing Human Bruch's Membrane: Implications for ECM Turnover", Investigative Ophthalmology & Visual Science, vol. 51, No. 5—7 pages (May 2010).
Lee et al., "Modulating the Transport Characteristics of Bruch's Membrane with Steroidal Glycosides and its Relevance to Age-Related Macular Degeneration (AMD)", Investigative Opthalmology & Visual Science, vol. 56, No. 13—16 pages (Dec. 2015).
Maurice et al., "Subretinal Pressure and Retinal Adhesion", Exp. Eye Res., vol. 12—6 pages (1971).
Moore et al., "Age-Related Variation in the Hydraulic Conductivity of Bruch's Membrane", Investigative Ophthalmology & Visual Science, vol. 36, No. 7—8 pages (Jun. 1995).
Owsley et al., "Delays in Rod-mediated Dark Adaptation in Early Age-related Maculopathy", Ophthalmology, vol. 108, No. 7—7 pages (Jul. 2001).
Owsley et al., "Effect of Short-Term, High-Dose Retinol on Dark Adaptation in Aging and Early Age-Related Maculopathy", Investigative Ophthalmology & Visual Science, vol. 47, No. 4—9 pages (Apr. 2006).
Ramrattan et al., "Morphometric Analysis of Bruch's Membrane, the Choriocapillaris, and the Choroid in Aging", Investigative Ophthalmology & Visual Science, vol. 35, No. 6—8 pages (May 1994).
Sakai et al., "Ocular Age Pigment "A2-E": An Unprecedented Pyridinium Bisretinoid", J. Am. Chem. Soc., vol. 118, No. 6—2 pages (1996).
Starita et al., "Hydrodynamics of Ageing Bruch's Membrane: Implications for Macular Disease", Exp. Eye Res., vol. 62 , No. 5—7 pages (1996).
Steinmetz et al., "Symptomatic abnormalities of dark adaptation in patients with age-related Bruch's membrane change", British Journal of Ophthalmology, vol. 77—6 pages (Sep. 1, 1993).
Tsuboi et al., "Effect of Plasma Osmolality and Intraocular Pressure on Fluid Movement Across the Blood-Retinal Barrier", Investigative Ophthalmology & Visual Science, vol. 29, No. 11—3 pages (Nov. 1988).
Witz, "Biological Interactions of $\alpha,\beta$-Unsaturated Aldehydes", Free Radical Biology & Medicine, vol. 7, No. 3—17 pages (1989).
Casswell et al., "Retinal pigment epithelial detachments in the elderly: classification and outcome", British Journal of Opthalmology, 1985, 69, 397-403.

\* cited by examiner

FIG. 3
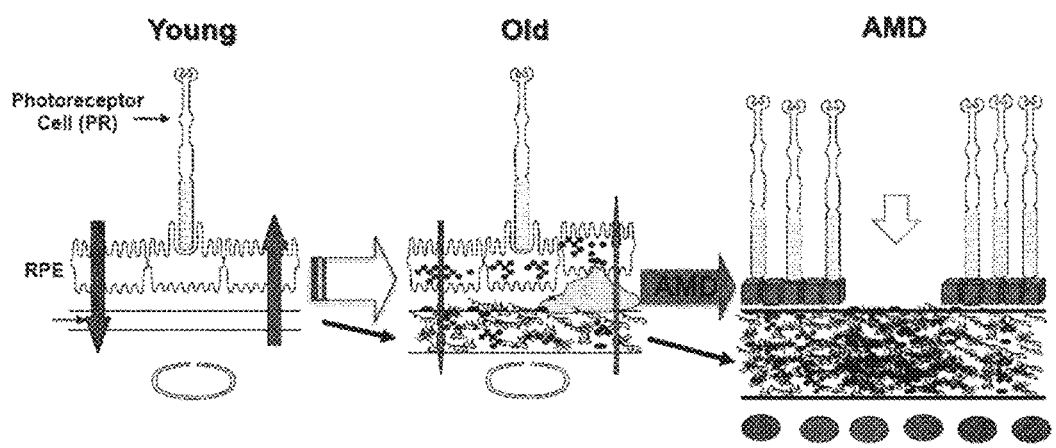
(A)
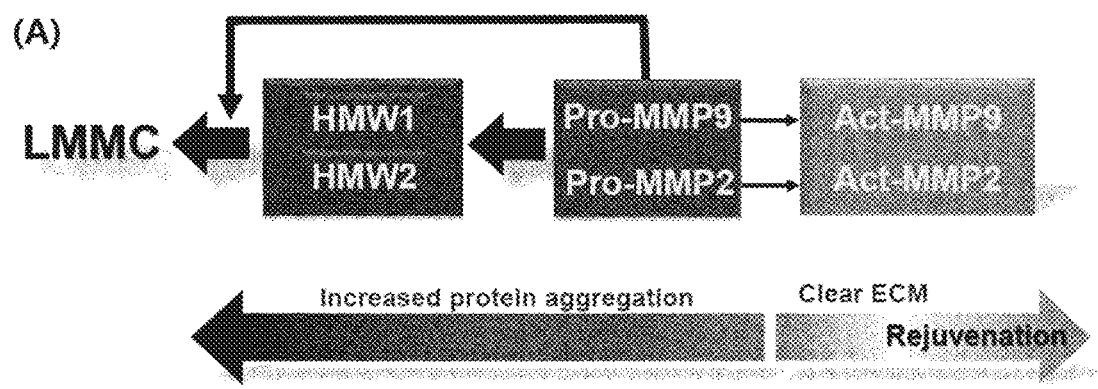
(B)
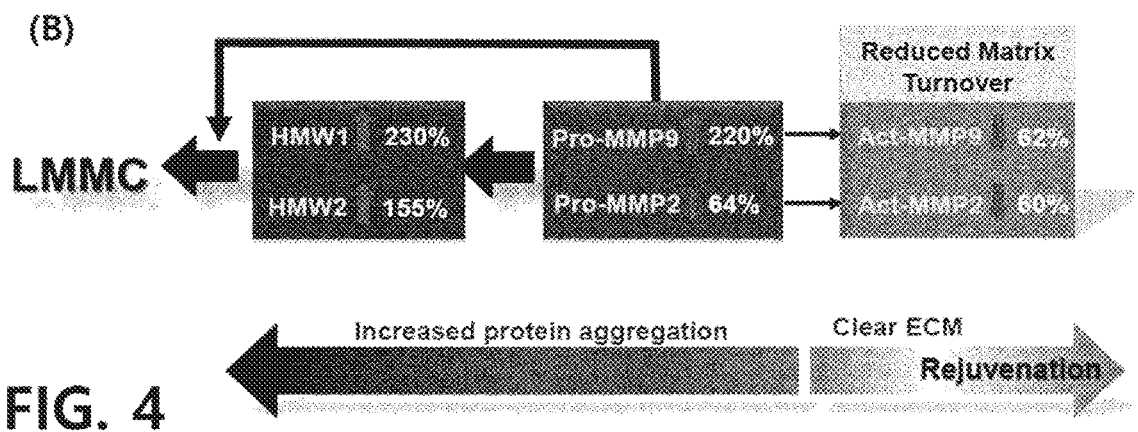
FIG. 4

A Summary of Kinetic constants:

| Lipid class | Red Ginseng extract | Sea cucumber extract |
|---|---|---|
| Cholesterol esters | $K_m$ = 0.1%; $V_{max}$ = 4.1ug | $K_m$ = 1.2%; $V_{max}$ = 4.6ug |
| Cholesterol | $K_m$ = 0.45%; $V_{max}$ = 0.69ug | $K_m$ = 0.62%; $V_{max}$ = 0.9ug |
| Triglycerides | $K_m$ = 0.13%; $V_{max}$ = 0.67ug | $K_m$ = 0.05%; $V_{max}$ = 0.58ug |
| Phosphatidylcholine | $K_m$ = 0.35%; $V_{max}$ = 111ug | X-50 = 1.3%; $V_{max}$ = 197ug |

FIG. 12

B Efficiency of lipid removal

| Lipid class | Red Ginseng | Sea cucumber |
|---|---|---|
| Cholesterol esters | ↑↑↑ | ↑ |
| Cholesterol | ↑ | ↑ |
| Triglycerides | ↑ | ↑↑ |
| Phosphatidyl choline | ↑ | ↑↑↑ |

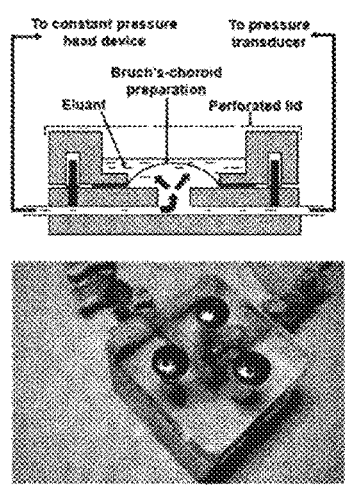
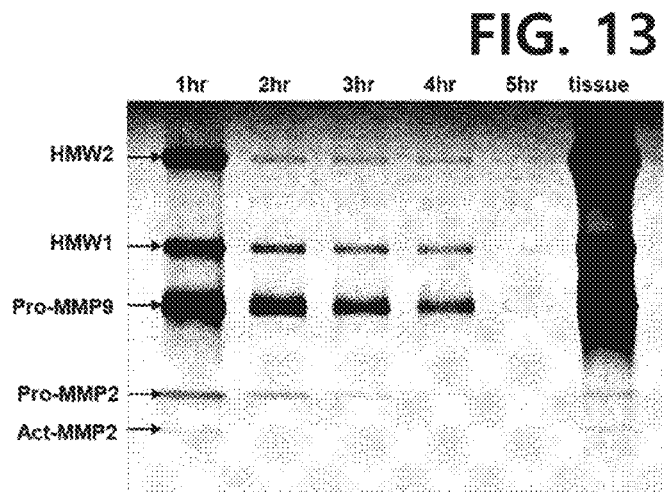
FIG. 13
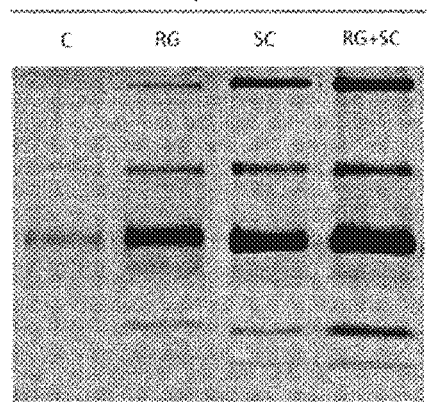
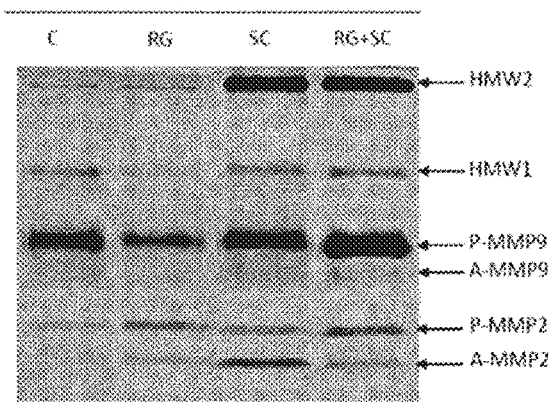
FIG. 14
C: Control; RG: 2.5% red ginseng; SC: 2.5% sea cucumber; RG+SC: 2.5% each red ginseng & sea cucumber.

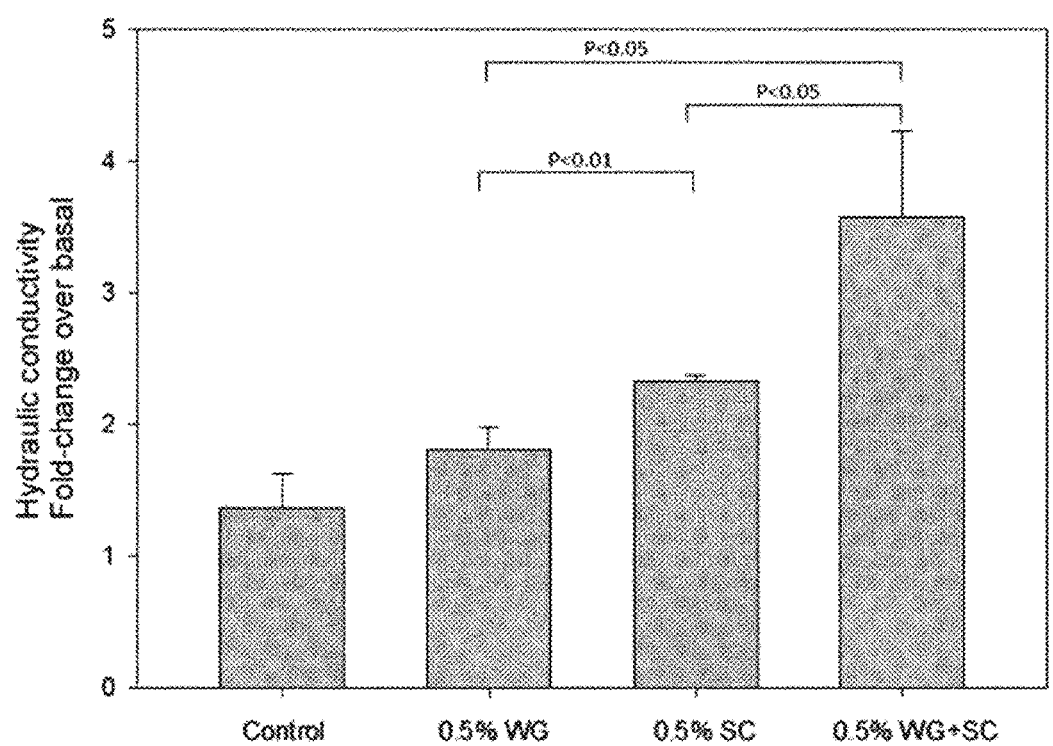
FIG. 17  C: Control; WG: white ginseng; SC: sea cucumber

METHOD OF TREATING BRUCH'S MEMBRANE HYPOFUNCTION DISEASE

TECHNICAL FIELD

The present invention relates to a composition for preventing or treating a Bruch's membrane hypofunction-related disease, which includes a composite extract of ginseng/red ginseng and a sea cucumber, and more particularly, to a composition for preventing, treating, or alleviating a Bruch's membrane hypofunction-related disease, which includes a composite extract of ginseng/red ginseng and a sea cucumber which has an effect of regenerating the Bruch's membrane of the eye and improving a transport function thereof.

BACKGROUND ART

Ginseng is one of the medicines traditionally used for the treatment of various diseases in Asian countries such as China, Korea, Japan, and the like. Ginseng saponin (ginsenoside), which is a major active ingredient of ginseng, is known to have various physiological activities such as anti-aging, anti-inflammation, antioxidant activity in the central nervous system, the cardiovascular system, and the immune system, antidiabetic activity, antitumor activity, and the like. To date, over 30 ginsenosides have been isolated and identified from ginseng saponins, and ginsenosides, which are glycosides containing aglycone having the dammarane skeleton, are mostly accounted for by ginsenosides Rb1, Rb2, Re, and Rd, which belong to the protopanaxadiol-based saponin, and ginsenosides Re and Rg1, which belong to the protopanaxatriol-based saponin.

Raw ginseng is called fresh ginseng, dried ginseng is called white ginseng, and steam and dried ginseng is called red ginseng. White ginseng is obtained by peeling fresh ginseng and drying the peeled ginseng in sunlight for 1 to 2 days, ginseng dried in a straight form without bending and folding is called straight ginseng, and thick tails which are bent and dried are called curved ginseng or half-curved ginseng according to the degree of bending. In addition, the dried fine roots of fresh ginseng are called fine root ginseng.

Sea cucumber is a generic term for sea cucumbers, which are echinoderms belonging to the class Holothuroidea and is the most healthy food called ginseng of the sea due to large contents of effective ingredients such as saponin as in ginseng, and the like. Sea cucumber is known to be a medication for supplementing body fluids which has been used in Eastern countries including China from old times, be highly effective against diabetes, asthma, and the like, and enable an individual to regain energy when suffering from energy loss and a state of collapse due to much sweating in summer as the temperature increases. In addition, a sea cucumber has a remarkable restoring force such that, when a part of the body is cut, the cut part is restored to its original state within three months, and new intestines are formed within one month even when the intestines are removed. Thus, in oriental medicine and home remedies, a sea cucumber is known to enhance the phagocytic ability of monocytes and macrophages of the human body to thus accelerate immune functions and be effective in wound healing.

Visual cells sense light that is present in the retina and enable an object to be recognized by transmitting information to the brain in a vision process. Visual cells are the most active part of metabolism in our body, and in this regard, it is essential to effectively deliver nutrients and remove waste. Since essential fatty acids, light, and a high concentration of oxygen are abundant in these cells, they are mostly damaged by free radicals. In this case, the retinal pigment epithelium (RPE) enables the outer segments of damaged visual cells to be continuously regenerated.

Visual cells and the RPE are provided with nutrients through blood circulation of the choroid. When nutrients supplied from blood are secreted from capillaries of the choroid, the nutrients must pass through the Bruch's membrane, which is an extracellular matrix, before reaching the RPE and visual cells. Nutrients such as glucose, oxygen, amino acids, and the like which have small sizes pass through the Bruch's membrane by simple passive diffusion, and vitamins, trace metals, lipids are bound to carrier proteins and then pass through the Bruch's membrane, which are then separated in the RPE. Conversely, waste products produced in visual cells and the RPE pass through the Bruch's membrane and are removed from the choroid. Most waste products are toxic, and thus are likely to damage the Bruch's membrane and may initiate an inflammatory response. Therefore, the ability of the Bruch's membrane to effectively transport materials is considered to be essential for the maintenance of normal vision and the survival of visual cells (see FIG. 1).

Due to aging, the thickness of the Bruch's membrane increases 2-fold to 3-fold, thus reducing diffusion gradients which allow the exchange between nutrients and waste products, and accordingly, the diffusion of materials through the Bruch's membrane becomes difficult. This results in deposition of proteo-lipid complexes and waste products discarded from the RPE on the membrane, increased cross-linking of collagen, and an increased amount of denatured collagen. In addition, glycation end-products of proteins and lipids produced by glycosylation (AGE; advanced protein glycation end-products, ALE; advanced lipid glycation end-products) increase (Handa et al. 1999), and the deposition of damaged or polymerized protein complexes also increases. Moreover, thiol groups exposed to normal or denatured proteins due to aging are trapped in the membrane as they form dimers or polymers through the oxidation process, leading to a reduction in free thiol groups. All these changes consequently interfere with the membrane transport capability, and adversely affect the function of the membrane in delivering nutrients and removing waste products (Holz et al. 1994) (see FIG. 2).

These aging-related changes are much more dramatic and severe in the case of age-related macular degeneration (AMD) wherein aging is a major cause of disease, and a reduction in the transport ability of the Bruch's membrane results in apoptosis of the RPE and visual cells, resulting in loss of eyesight (see FIG. 3).

It has been clinically reported that the aging of the Bruch's membrane in the elderly reduces scotopic thresholds due to insufficient regeneration of vitamin A (Steinmetz et al. 1993; Owsley et al. 2001), and in some countries, prescription is currently done by adding a metal and an antioxidant to vitamin A. However, this method has two problems. The first problem is that, since only a specific nutrient is added, essential nutrients other than that are still deficient, and the second problem is that, when a metal is added into the Bruch's membrane having a deteriorated transport function, the concentration of the metal in the Bruch's membrane increases and the metal continues to be deposited on the membrane, and damage caused thereby becomes much bigger. According to the age-related eye disease study (AREDS), which is an American AMD clinical trial that has been carried out for more than 10 years, the effect of a composition consisting of vitamins and mineral additives has not yet been proven (Kassof et al. 2001).

The ideal solution for vision impairment due to aging, including age-related macular degeneration, facilitates the transport capability of the Bruch's membrane, thus enabling the membrane to be supplied with all necessary nutrients present in the plasma.

As a result of having made intensive efforts to develop a treatment method capable of addressing fundamental causes of aging-related eye hypofunction including age-related macular degeneration, the inventors of the present invention discovered that a composite extract of ginseng/red ginseng and a sea cucumber had an excellent effect of enhancing a transport ability of the Bruch's membrane and regenerating the Bruch's membrane, and confirmed that the composite extract was able to be used as a composition for preventing or treating a disease caused by Bruch's membrane hypofunction, thus completing the present invention.

REFERENCE DOCUMENTS

[1] Bird A C & Marshall J. Retinal pigment epithelial detachments in the elderly. (1986) Trans. Soc. Ophthal. UK. 105: 674-682.

[2] Birkedal-Hansen H, Moore W G, Bodden M K, Windsor L J, Birkendal-Hansen B, DeCarlo A, Engler J A. (1993) Matrix metalloproteinases: a review. Crit. Rev. Oral Biol. Med. 4: 197-250.

[3] Bok D. Retinal photoreceptor-pigment epithelium interactions. Friedenwald Lecture. Invest. Ophthalmol. Vis. Sci. 1985; 26: 1659-94.

[4] Bui B V, Kalloniatis M and Vingrys A J. The contribution of glycolytic and oxidative pathways to retinal photoreceptor function. Invest. Ophthalmol. Vis. Sci 2003. 44: 2707-2715.

[5] Chihara E and Nao-I N. Resorption of subretinal fluid by transepithelial flow of the retinal pigment epithelium. Graefes Arch Klin Exp Ophthalmol. 1985; 223: 202-204.

[6] Emi K, Pederson J E, Toris C B. Hydrostatic pressure of the suprachoroidal space. Invest. Ophthalmol. Vis. Sci. 1989; 30: 233-238.

[7] Esterbauer H, Schaur R J and Zollner H. Chemistry and biochemistry of 4-hydroxynonenal, malonaldehyde and related aldehydes. Free Radic. Biol. Med. 1991; 11: 81-128.

[8] Frambach D A and Marmor M F. The rate and route of fluid resorption from the subretinal space of the rabbit. Invest. Ophthalmol. Vis. Sci. 1982; 22: 292-302.

[9] Guo L, Hussain A A, Limb G A & Marshall J. Age-dependent variation in the metalloproteinase activity of Bruch's membrane and choroid. (1999) Invest. Ophthalmol. Vis. Sci. 40: 2676-2682.

[10] Handa J T, Verzijl N, Matsunaga H, Aotaki-Keen A, Lutty G A, to Koppele J M, Miyata T and Hjelmeland L M. Increase in the advanced glycation end-product pentosidine in Bruch's membrane with age. Invest. Ophthalmol. Vis. Sci. 1999; 40: 775-779.

[11] Holz F G, Sheraidah G S, Pauleikhoff D and Bird A C. Analysis of lipid deposits extracted from human macular and peripheral Bruch's membrane. Arch. Ophthalmol. 1994; 112: 402-406.

[12] Hughes B A, Miller S S and Machen T E. The effects of cAMP on fluid absorption and ion transport across frog retinal pigment epithelium: measurements in the open-circuit state. J. Gene Physiol. 1984; 83: 875-899.

[13] Hussain A A, Rowe L, Marshall J. (2002) Age-related alterations in the diffusional transport of amino acids across the human Bruch's-choroid complex. Journal of the Optical Society of America, A, Optics, Image Science, & Vision. 19(1): 166-72.

[14] Hussain A A, Starita C, and Marshall J. (2004) Chapter IV. Transport characteristics of ageing human Bruch's membrane: Implications for AMD. In: Focus on Macular Degeneration Research, (Editor O. R. Ioseliani). Pages 59-113. Nova Science Publishers, Inc. New York.

[15] Hussain A A, Starita C, Hodgetts A, Marshall J. (2010) Macromolecular characteristics of ageing human Bruch's membrane: implications for age-related macular degeneration (AMD). Exp. Eye Res. 90:703-710.

[16] Hussain A A, Lee Y, Marshall J. (2010) High molecular weight gelatinase species of human Bruch's membrane: compositional analyses and age-related changes. Invest. Ophthalmol. Vis. Sci. 51:2363-71.

[17] Hussain A A, Lee Y, Zhang J J, Marshall J. (2011) Disturbed matrix metalloproteinase activity of Bruch's membrane in age-related macular degeneration (AMD). Invest. Ophthalmol. Vis. Sci. 52:4459-66.

[18] Hussain A A, Lee Y, Zhang J J, Francis P T, Marshall J. 2016. Disturbed matrix metalloproteinase (MMP) pathway in both age-related macular degeneration (AMD) and Alzheimer's disease (AD). J. Neurodegenerative diseases (in Press).

[19] Karwatowski W S S, Jefferies T E, Duance V C, Albon J, Bailey A J & Easty D L. Preparation of Bruch's membrane and analysis of the age related changes in the structural collagens. (1995) Brit. J. Ophthalmol. 79: 944-952.

[20] Kassof A, Kassoff J, Buehler J, et al., A randomized, placebo-controlled, clinical trial of high dose supplementation with vitamins C and E, beta carotene, and zinc for age-related macular degeneration and vision loss: AREDS report No. 8. Arch Ophthalmol. 2001; 119:1417-36.

[21] Kumar A, El-Osta A, Hussain A A, Marshall J. (2010) Increased sequestration of matrix metalloproteinases in ageing human Bruch's membrane: implications for ECM turnover. Invest. Ophthalmol. Vis. Sci. 51:2664-70.

[22] Lee Y, Hussain A A, SeokJ-H, Kim S-H, Marshall J. (2015) Modulating the transport characteristics of Bruch's membrane with steroidal glycosides and its relevance to age-related macular degeneration (AMD). Invest. Ophthalmol. Vis Sci. 56(13):8403-18.

[23] Maurice D M, Salmon J and Zauberman H. Subretinal pressure and retinal adhesion. Exp. Eye Res. 1971; 12: 212-217.

[24] Moore D J, Hussain A A, Marshall J. (1995). Age-related variation in the hydraulic conductivity of Bruch's membrane. Invest. Ophthalmol. Vis. Sci. 36(7): 1290-7.

[25] Owsley C, Jackson G R, White M, Feist R and Edwards D. Delays in rod mediated dark adaptation in early age-related maculopathy. Ophthalmol. 2001; 108: 1196-1202.

[26] Owsley C, McGwin G, Jackson G R, Heinburger D C, Piyathilake C J, Klein R, White M F, Kallies K. Effect of short term, high-dose retinol on dark adaptation in age and age-related maculopathy. Invest. Ophthalmol. Vis. Sci. 2006. 47(4):1310-8.

[27] Ramratten R S, van der Schaft T L, Mooy C M, de Bruijn W C, Mulder P G H and de Jong P T V M. Morphometric analysis of Bruch's membrane, the choriocapillaris and the choroid in ageing. Invest. Ophthalmol. Vis. Sci. 1994; 35: 2857-2864.

[28] Sakai N, Decatur J, Nakanishi K and Eldred G E. Ocular age pigment 'A2E': an unprecedented pyridinium bisretinoid. J Am. Chem. Soc. 1996; 118: 1559-1560.

[30] Steinmetz R L, Haimovici R, Jubb C, Fitzke F W, Bird A. Symptomatic abnormalities of dark adaptation in patients with age-related Bruch's membrane change. Br. J. Ophthalmol. 1993; 77:549-554.

[31] Tsuboi S and Pederson J E. Effect of plasma osmolality and intraocular pressure on fluid movement across the blood-retinal barrier. Invest. Ophthalmol. Vis. Sci. 1988; 29: 1747-1749.

[32] Witz G. Biological interactions of a,b-unsaturated aldehydes. Free Radic. Biol. Med. 1989; 7: 333-349.

DESCRIPTION OF EMBODIMENTS

Technical Problem

An object of the present invention is to provide a pharmaceutical composition for preventing, delaying, or treating a Bruch's membrane hypofunction-related disease which includes, as an active ingredient, a composite extract of ginseng and a sea cucumber, or a fraction thereof; or a composite extract of red ginseng and a sea cucumber, or a fraction thereof.

Another object of the present invention is to provide a health functional food composition for preventing, delaying, or alleviating a Bruch's membrane hypofunction-related disease which includes, as an active ingredient, a composite extract of ginseng and a sea cucumber, or a fraction thereof; or a composite extract of red ginseng and a sea cucumber, or a fraction thereof.

Still another object of the present invention is to provide a health functional food composition for improving eye health which includes, as an active ingredient, a composite extract of ginseng and a sea cucumber, or a fraction thereof; or a composite extract of red ginseng and a sea cucumber, or a fraction thereof.

Yet another object of the present invention is to provide a method of preventing, delaying, or treating a Bruch's membrane hypofunction-related disease, including administering, to a subject, a composition including, as an active ingredient, a composite extract of red ginseng and a sea cucumber, or a fraction thereof; or a composite extract of ginseng and a sea cucumber, or a fraction thereof.

Technical Solution

The present invention has been made to address the above-described problems, and there is provided a pharmaceutical composition for preventing, delaying, or treating a Bruch's membrane hypofunction-related disease, which includes, as an active ingredient, a composite extract of ginseng and a sea cucumber, or a fraction thereof; or a composite extract of red ginseng and a sea cucumber, or a fraction thereof.

The term "ginseng" as used herein includes *Panax ginseng, P. quiquefolius, P. notoginseng, P. japonicus, P. trifolium, P. pseudoginseng, P. vietnamensis*, and *P. quinquefolium*, but the present invention is not limited thereto. In particular, the term "red ginseng" as used herein refers to ginseng produced by heating fresh ginseng through steam or sun-drying, preferably steam, and more preferably ginseng obtained by steaming fresh ginseng at 98° C. to 100° C. and drying the steamed ginseng at about 60° C. Although the present invention is described as being applied to a ginseng extract or a red ginseng extract, the present invention may be applied to various processed forms of ginseng, for example, fresh ginseng, fine root, white ginseng, taekuk ginseng, black ginseng, dextrinized ginseng, enzymatically treated ginseng, fermented ginseng, and fermented red ginseng, but is not limited thereto.

The term "sea cucumber" as used herein refers to marine invertebrates belonging to the *phylum Echinodermata*, the class Holothuroidea, and examples thereof may include, but are not limited to, scaly sea cucumber, the species *Lipotrapeza japonica*, the species *Sclerodactyla multipes, Cucumaria frondosa japonica*, the species *Plesiocolochirus inornatus*, and the like which belong to the order Dendrochirotacea; the species *Apostichopus japonicus, Holothuria hilla, Holothuria argus, Holothuria hilla*, and the like which belong to the order Aspidochirotida; Synaptidae, *Polycheira rufescens*, and the like which belong to the order Apodida; and the species *Paracaudina chilensis, Molpadia oolitica*, and the like which belong to the order Molpadida. The above sea cucumber is recommended as a promoting and tonic agent, for pregnant women and weak women, and as a healthy food for patients with hypertension, arteriosclerosis, diabetes, or obesity, but the effect thereof on eye aging-related diseases has never been known. The term "extract" as used herein refers to an extract itself and all forms of extracts capable of being formed using an extract, such as an extract obtained by extracting ginseng/red ginseng or a sea cucumber, a dried product obtained by drying the ginseng, the red ginseng, or the sea cucumber, a diluted solution or concentrate of the extract, a dried product obtained by drying the extract, a crude purified product or purified product of the extract, a mixture thereof, and the like. The extract or fraction of the present invention may be used, preferably in a liquid form after extraction.

In the composite extract of ginseng/red ginseng and a sea cucumber of the present invention, the extraction of the ginseng/red ginseng and a sea cucumber is not particularly limited and may be performed according to a method commonly used in the art. Non-limiting examples of the extraction method may include hot-water extraction, ultrasonic extraction, filtration, and reflux extraction, and one of these methods or a combination of two or more of these methods may be used.

In the present invention, the type of extraction solvent used for extracting ginseng/red ginseng and a sea cucumber is not particularly limited, and any solvent known in the art may be used. Non-limiting examples of the extraction solvent may include water, an alcohol, and mixed solvents thereof, and when an alcohol is used as a solvent, preferably a $C_1$-$C_4$ alcohol, more preferably a $C_1$ to $C_2$ lower alcohol, and more preferably an aqueous 80% ethanol solution may be used, but the present invention is not limited thereto. The sea cucumber extract of the present invention may be, preferably, water or an ethanol extract.

In the present invention, when the ginseng/red ginseng and a sea cucumber is extracted by hot-water extraction, the extraction may be repeatedly performed one to five times, more preferably three times, but the present invention is not limited thereto. The extraction solvent may be added in an amount that is 0.1 to 100 times, preferably 0.3 to 5 times the weight of dried ginseng/red ginseng and a dried sea cucumber. The extraction temperature may range from 20° C. to 130° C., but the present invention is not limited thereto. In addition, the extraction time may range from 30 minutes to 48 hours, but the present invention is not limited thereto.

In a method of preparing the extract of ginseng/red ginseng and a sea cucumber of the present invention, concentration under reduced pressure may be performed using a vacuum decompression concentrator or a vacuum rotary evaporator, but the present invention is not limited thereto.

In addition, the drying process may be performed by natural drying, hot-air drying, freeze drying, drying under reduced pressure, vacuum drying, boiling drying, spray drying, or freeze drying, but the drying method is not particularly limited as long as it is any method known in the art which is used to remove moisture.

In the extraction or drying of a sea cucumber of the present invention, the outer skin and intestine of a sea cucumber may be completely extracted or dried or may be separately extracted or dried, and extracts or dried products of the outer skin and intestine of a sea cucumber may be respectively used or a mixture thereof may also be used.

In a specific embodiment of the present invention, red ginseng was produced by washing and steaming fresh ginseng, followed by primary drying at 60° C. to 70° C. for 12 hours to 20 hours and sunlight drying, and the resulting product was extracted four times with hot water as a solvent, followed by filtration, cooling, purification by centrifugation, and vacuum concentration, thereby obtaining an extract.

In another specific embodiment of the present invention, a dried sea cucumber was ground to prepare sea cucumber powder, 70% ethanol was added as an extraction solvent thereto, the resulting product was extracted for about 3 hours to about 6 hours, and the ethanol was removed therefrom in a vacuum, thereby obtaining an extract.

The term "fraction" as used herein refers to a resulting product obtained by fractionation for separating a specific component or a specific component group from a mixture including various constituent components.

In the present invention, a fractionation method used to obtain the fraction is not particularly limited and may be performed according to a method commonly used in the art. As a non-limiting example of the fractionation method, there is a method of obtaining a fraction from an extract obtained by treating an extract obtained by extracting ginseng/red ginseng and a sea cucumber with a predetermined solvent.

In the present invention, the type of fractionation solvent used to obtain the fraction is not particularly limited, and any solvent known in the art may be used. Non-limiting examples of the fractionation solvent may include polar solvents such as water and alcohols; and non-polar solvents such as ethyl acetate, chloroform, and dichloromethane. One of these fractionation solvents or a mixture of two or more of these solvents may be used. When an alcohol is used as the fractionation solvent, preferably, a $C_1$-$C_4$ alcohol may be used.

The active ingredient of the present invention enhances the transport function of the Bruch's membrane to thereby prevent the onset of a Bruch's membrane hypofunction-related disease, delay the progression of the disease, or treat the disease.

The active ingredient of the present invention may improve the hydraulic conductivity of the Bruch's membrane, improve a material diffusion function of the Bruch's membrane, or improve a transport function of the Bruch's membrane by removing a protein or lipid bound to or trapped in the Bruch's membrane.

The active ingredient of the present invention may regenerate the Bruch's membrane and enhance the function of the Bruch's membrane to thereby prevent the onset of a Bruch's membrane hypofunction-related disease, delay the progression of the disease, or treat the disease.

The active ingredient of the present invention may regenerate the Bruch's membrane and enhance the function of the Bruch's membrane by removing a high molecular weight complex (HMW) or lipid component bound to or deposited on the Bruch's membrane.

In addition, the active ingredient of the present invention may regenerate the Bruch's membrane and enhance the function of the Bruch's membrane by secreting pro-MMP2, pro-MMP9, active MMP2, and active MMP9 from a matrix of the Bruch's membrane.

In addition, the active ingredient of the present invention may regenerate the Bruch's membrane and enhance the function of the Bruch's membrane by activating the secretion of active MMP from retinal epithelial cells (RPEs).

As such, the composite extract of ginseng/red ginseng and a sea cucumber of the present invention degrades materials that age the Bruch's membrane and cause the loss of function thereof by being polymerized in the Bruch's membrane, and secretes nutrients and waste products such as proteins or lipids trapped in or bound to the matrix of the Bruch's membrane, thereby helping supply nutrients to the eyes and discharge waste products. In addition, the active ingredient of the present invention is involved in the regeneration of a function of the Bruch's membrane by recovering the function of an enzyme through the secretion of MMP, and increases the hydraulic conductivity of the eyes and the degree of diffusion of materials, thereby not only preventing aging of the retina, but also regenerating the function of the retina, whereby the loss of retinal function due to aging is prevented, delayed, or treated.

The term "prevention" or "delaying" as used herein means all actions that inhibit or delay the onset of a disease occurring due to Bruch's membrane hypofunction via administration of the composition of the present invention to a subject.

The term "treatment" as used herein means all actions that alleviate or beneficially change symptoms of a disease occurring due to Bruch's membrane hypofunction via administration of the composition of the present invention to a subject.

The term "alleviation" as used herein means all actions that decrease at least the degree of parameters related to conditions being treated, e.g., symptoms.

In the pharmaceutical composition of the present invention, the composite extract of ginseng/red ginseng and a sea cucumber, or a fraction thereof may be included in an amount of preferably 0.1 wt % to 99.99 wt %, more preferably 10 wt % to 99.99 wt %, and even more preferably 50 wt % to 99.99 wt %, with respect to a total weight of the pharmaceutical composition. Within the above ranges, the effect of the composite extract of ginseng/red ginseng and a sea cucumber, or a fraction thereof on enhancing the transport function of the Bruch's membrane, regenerating the Bruch's membrane, and enhancing the function of the Bruch's membrane is sufficiently realized, and thus it is more suitable for achieving the objectives of the present invention.

The pharmaceutical composition of the present invention may further include a pharmaceutically acceptable carrier, in addition to the composite extract of ginseng/red ginseng and a sea cucumber, or a fraction thereof as an active ingredient.

The expression "pharmaceutically acceptable" as used herein means commonly used in the pharmaceutical field without irritating a living organism when administered and hindering the biological activity and properties of a compound to be administered.

The pharmaceutical composition of the present invention may be formulated together with the carrier to be used as foods, medicines, feed additives, drinking water additives, and the like. In the present invention, the type of the carrier is not particularly limited and any carrier commonly used in the art may be used. Non-limiting examples of such carriers include saline, sterilized water, Ringer's solution, buffered saline, albumin injection solution, lactose, dextrose, sucrose, sorbitol, mannitol, xylitol, erythritol, maltitol, maltodextrin, glycerol, and ethanol. One of these carriers or a mixture of two or more of these carriers may be used.

In addition, as needed, other pharmaceutically acceptable additives such as an excipient, a diluent, an antioxidant, a buffer, a bacteriostat, or the like may be added to the pharmaceutical composition of the present invention, and a filler, an extender, a wetting agent, a disintegrating agent, a dispersant, a surfactant, a binder, a lubricant, or the like may be additionally added.

The pharmaceutical composition of the present invention may be formulated into various preparations suitable for oral administration or parenteral administration. Non-limiting examples of such preparations for oral administration include troches, lozenges, tablets, aqueous suspensions, oily suspensions, prepared powders, granules, emulsions, hard capsules, soft capsules, syrups, and elixirs.

To formulate the pharmaceutical composition of the present invention for oral administration, a binder such as lactose, saccharose, sorbitol, mannitol, starch, amylopectin, cellulose, gelatin, or the like; an excipient such as dicalcium phosphate or the like; a disintegrating agent such as corn starch, sweet potato starch, or the like; a lubricant such as magnesium stearate, calcium stearate, sodium stearyl fumarate, polyethylene glycol wax, or the like; or the like may be used, and a sweetener, a fragrance, syrup, or the like may also be used.

Moreover, in the case of capsules, liquid carriers such as fatty oils other than the aforementioned materials, or the like may be additionally used.

Non-limiting examples of the parenteral preparation include injections, suppositories, respiratory inhalation powders, aerosol preparations for spraying, ointments, powders for application, oils, and creams.

To formulate the pharmaceutical composition of the present invention for parenteral administration, sterilized aqueous solutions, non-aqueous solvents, suspensions, emulsions, freeze-dried preparations, agents for external application, or the like may be used, and as the non-aqueous solvents and the suspensions, propylene glycol, polyethylene glycol, a vegetable oil such as olive oil, an injectable ester such as ethyl oleate or the like may be used.

More specifically, when the pharmaceutical composition of the present invention is formulated into an injection, the composition of the present invention may be mixed with a stabilizer or a buffer in water to prepare a solution or a suspension, followed by preparation into an ampoule or vial unit dosage form. When the pharmaceutical composition of the present invention is formulated into an aerosol preparation, a propellant or the like may be added together with an additive such that a water-dispersed concentrate or wet powder is dispersed.

In addition, when the pharmaceutical composition of the present invention is formulated into an ointment, cream, or the like, formulation may be carried out using a carrier such as animal oil, vegetable oil, wax, paraffin, starch, tragacanth, a cellulose derivative, polyethylene glycol, silicon, bentonite, silica, talc, zinc oxide, or the like may be used.

The pharmaceutically effective amount and effective dosage of the pharmaceutical composition of the present invention may be varied depending on the formulation method, administration method, administration time and/or administration routes of the pharmaceutical composition, and may be varied depending on various factors including the type and degree of response to be achieved via administration of the pharmaceutical composition, the type, age, and body weight of a subject to which the pharmaceutical composition is administered, general health conditions, the symptom or severity of disease, gender, diet, excretion, and other drug compositions used together simultaneously or separately in the corresponding subject, and similar factors known in the medical field. An effective dosage level for the desired treatment may be readily determined and prescribed by those of ordinary skill in the art.

The dosage of the pharmaceutical composition of the present invention for a more preferably effect may range from, preferably 0.01 mg/kg/day to 1,000 mg/kg/day, and more preferably 1 mg/kg/day to 500 mg/kg/day. The pharmaceutical composition may be administered once or multiple times a day. Thus, the dosage is not intended to limit the scope of the present invention in any way.

The administration route and administration method of the pharmaceutical composition of the present invention may be independent of each other, the method is not particularly limited, and any administration route and administration method may be used as long as they enable the pharmaceutical composition to reach the target site. The pharmaceutical composition may be administered orally or parenterally.

The parenteral administration may be, for example, intravenous administration, intraperitoneal administration, intramuscular administration, transdermal administration, subcutaneous administration, or the like, and the composition may also be applied or sprayed onto a disease site or inhaled, but the present invention is not limited thereto.

The pharmaceutical composition of the present invention may preferably be administered orally or transdermally.

The composition of the present invention may further include one or more selected from the group consisting of amino acids, antioxidants, vitamins, minerals, metal substances, lutein, astaxanthin, zeaxanthin, and bilberry extracts to enhance an effect of preventing, delaying, or treating a Bruch's membrane hypofunction-related disease. More particularly, the vitamins or minerals may be vitamin C, vitamin E, beta-carotene, zinc oxide, or cupric oxide which are effective in improving eye function, but the present invention is not limited thereto.

In the present invention, the Bruch's membrane hypofunction-related disease may be age-related macular degeneration (AMD), Sorsby's fundus dystrophy, Malattia Levintanese (ML), Stargardt disease, Best's vitelliform retinal dystrophy, or Doyne's honeycomb retinal dystrophy (DHRD), but the present invention is not limited thereto.

The present invention also provides a health functional food composition for preventing, delaying, or alleviating a Bruch's membrane hypofunction-related disease, including, as an active ingredient, the composite extract of ginseng and a sea cucumber, or a fraction thereof; or the composite extract of red ginseng and a sea cucumber, or a fraction thereof.

The present invention also provides a health functional food composition for enhancing eye health, including, as an active ingredient, the composite extract of ginseng and a sea cucumber, or a fraction thereof; or the composite extract of red ginseng and a sea cucumber, or a fraction thereof.

In the health functional food composition of the present invention, the composite extract of ginseng/red ginseng and a sea cucumber, or a fraction thereof, the efficacy thereof, and the like are the same as described above with regard to the pharmaceutical composition of the present invention.

When the health functional food composition of the present invention is used as a food additive, the composition may be directly added or may be used along with other foods or food ingredients and may be appropriately used according to a general method.

The type of food is not particularly limited and includes all foods in a general sense. Non-limiting examples of foods to which the material may be added may include meat, sausage, bread, chocolate, candies, snacks, confectionaries, pizza, ramen, other noodles, gums, dairy products including ice cream, various soups, beverages, tea, drinks, alcoholic beverages, and vitamin complexes.

When the health functional food composition of the present invention is a beverage composition, the beverage composition may include additional ingredients such as various flavoring agents, natural carbohydrates, or the like as in general beverages. Non-limiting examples of the natural carbohydrates may include monosaccharides such as glucose and fructose; disaccharides such as maltose and sucrose; natural sweeteners such as dextrin and cyclodextrin; and synthetic sweeteners such as saccharin and aspartame. A ratio of the added additional ingredients may be appropriately selected and determined by those of ordinary skill in the art.

In addition, the health functional food composition of the present invention may include various nutrients, vitamins, electrolytes, a flavoring agent, a colorant, pectic acid and a salt thereof, alginic acid and a salt thereof, organic acids, a protective colloidal thickening agent, a pH adjusting agent, a stabilizer, a preservative, glycerin, alcohols, carbonating agents used in carbonated beverages, or the like. In addition, the health functional food composition of the present invention may include pulp for preparing natural fruit juices, fruit beverages, vegetable beverages, or the like. These ingredients may be used alone or a combination of two or more of these ingredients may be used. A ratio of these additives may also be appropriately selected by those of ordinary skill in the art.

The present invention also provides a method of preventing, delaying, or treating a Bruch's membrane hypofunction-related disease, including administering, to a subject, the composition including, as an active ingredient, a composite extract of red ginseng and a sea cucumber, or a fraction thereof; or a composite extract of ginseng and a sea cucumber, or a fraction thereof.

Advantageous Effects of Invention

A composite composition according to the present invention has an effect of delaying or recovering eye aging by improving a transport function of the Bruch's membrane and accelerating the regeneration of the Bruch's membrane through the removal of deposited lipid components and the like, and thus is effective for the prevention or treatment of various diseases occurring due to Bruch's membrane hypofunction according to aging, including age-related macular degeneration (AMD) and can maintain the eye health of normal people and address problems due to a reduction in the transport of vitamins, metals, and antioxidants which is caused by aging.

BRIEF DESCRIPTION OF DRAWINGS

FIG. 3 is a diagram illustrating a change in the Bruch's membrane due to aging and a dramatic change in patients with macular degeneration.

FIG. 4 illustrates the MMP action mechanism for aging and regeneration of the Bruch's membrane and an abnormal MMP action mechanism in patients with macular degeneration.

FIG. 12 is a set of tables showing kinetic constants (A) and a relative efficiency thereof (B), showing the effect of a red ginseng extract and sea cucumber extract of the present invention on secreting various kinds of lipids present in the Bruch's membrane.

FIG. 13 illustrates results of removing free MMPs from a human Bruch's membrane.

FIG. 14 illustrates the results showing the effects of a red ginseng extract, a sea cucumber extract, and a composite extract thereof of the present invention on removing MMPs bound to a human Bruch's membrane.

FIG. 17 illustrates results showing a synergistic effect of a composite extract of ginseng and a sea cucumber on enhancing the transport function of the Bruch's membrane.

BEST MODE

Figure 1:
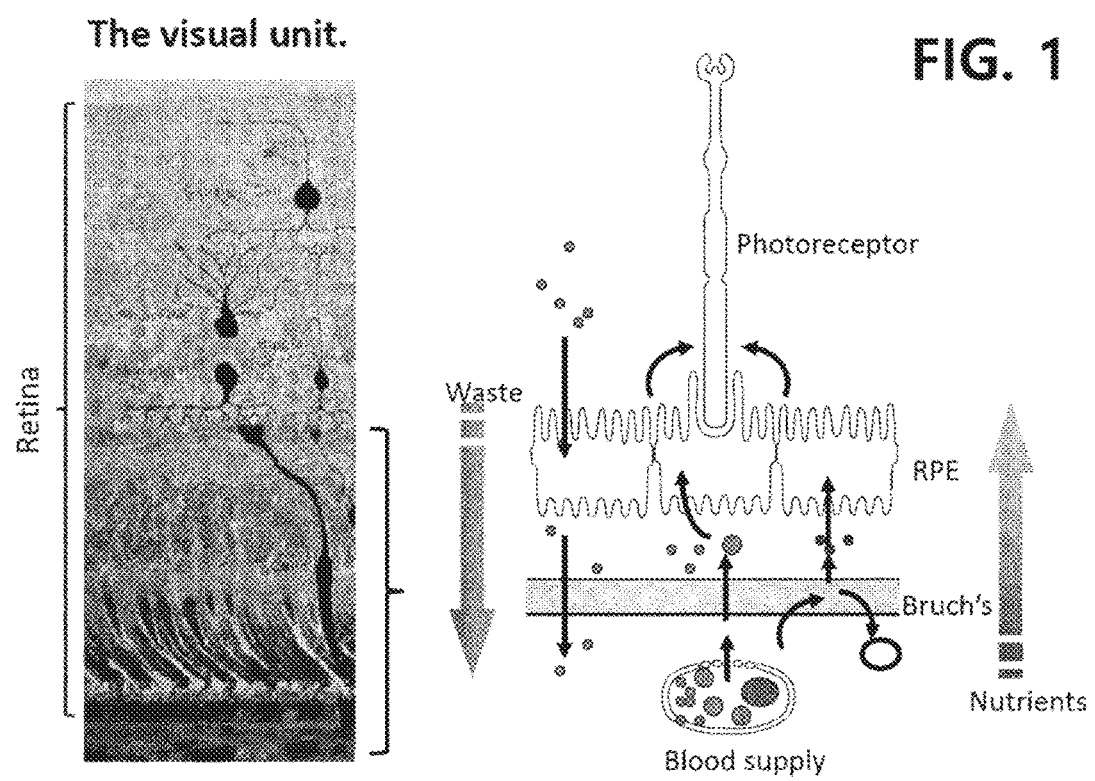
FIG. 1 illustrates a cross-sectional image of a human retina and components of visible light modulation (phototransduction).
Figure 2:
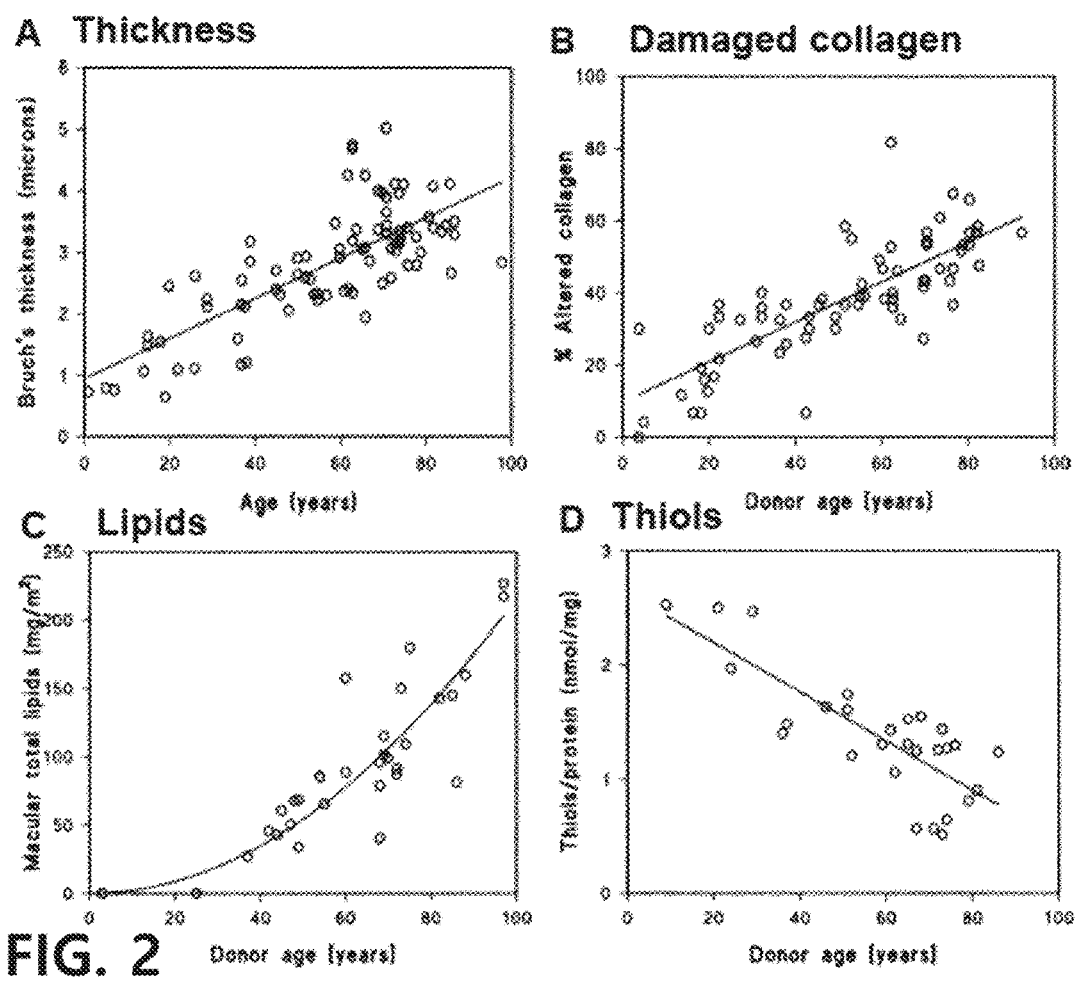
FIG. 2 is a set of graphs showing structural changes of the Bruch's membrane due to aging, wherein the thickness of the Bruch's membrane is increased 2-3-fold (A), the amount of damaged or denatured collagen is increased (B), major lipid substances such as cholesterol ester were exponentially increased (C), and the number of free thiol groups was decreased, leading to protein aggregation (D).

Hereinafter, the present invention will be described in more detail.

Degenerative changes in the transport function of the Bruch's membrane resulting from aging cause visual impairment in the elderly, and cause aging-related macular degeneration (AMD), which leads to eyesight loss in severe cases.

A number of studies have shown that aging has a severe adverse effect on the material transport capacity and waste removal processes of the Bruch's membrane (Hussain et al., 2002; 2004; 2010; Starita et al. 1996; Moore et al. 1995; Moore and Clover, 2001), and it is known that waste products accumulated in the Bruch's membrane, which increases in thickness due to aging, are composed of lipids and denatured proteins. In addition, the fundamental cause of waste accumulation in the Bruch's membrane was found to be due to the inability of the proteolytic enzyme called matrix metalloproteinases (MMPs) to play a role in the regeneration of the Bruch's membrane.

An MMP is a proteolytic enzyme that is secreted from the RPE into the Bruch's membrane in the form of a pro-form that is inert. The small peptide is removed from this precursor to become the active form, active MMP2 and active MMP9. Activated MMP2 and MMP9 enzymes are capable of degrading most of the extracellular matrix constituents through the activation process and remove damaged constituents and replace them with new materials. The mechanism of regeneration of this membrane plays a role in maintaining the structure and function of the Bruch's membrane in a healthy state. It has been shown, however, that the amounts of activated forms of MMP2 and MMP9 are reduced due to aging of the Bruch's membrane (Guo et al., 1999), and that the amounts of activated MMP2 and MMP9 in the Bruch's membrane of patients with macular degeneration were reduced by about 60% compared to the similar average age groups (Hussain et al., 2011).

Specifically, the MMP action mechanism according to aging is illustrated in FIG. 4. The precursor forms pro-MMP2 and pro-MMP9 form high molecular weight complexes (HMW), called HMW 1 and HMW 2, in the Bruch's membrane through polymerization. In addition, these materials are combined with other pro-MMP2 and pro-MMP9 molecules to form larger and larger macromolecular substances called large macromolecular complexes (LMMC) (Kumar et al., Hussain et al 2010). When the synthesis of such a polymer material increases due to aging, the polymer compound is trapped in or bound to the matrix, and pro-MMP and active MMP are also trapped in the membrane and cannot be used. As a result, the amount of free MMP required for regeneration of the membrane is reduced, so that the membrane is not decomposed and regenerated normally. As a result, a considerable amount of waste products accumulates, resulting in deterioration of the transport capability of the Bruch's membrane.

To confirm changes in the transport function of the Bruch's membrane due to aging, evaluation was performed on the macular part that plays a role in central vision and the peripheral part of eyes of 56 normal individuals and 11 patients with macular degeneration, aged between 1 year old and 96 years old.

Figure 5:
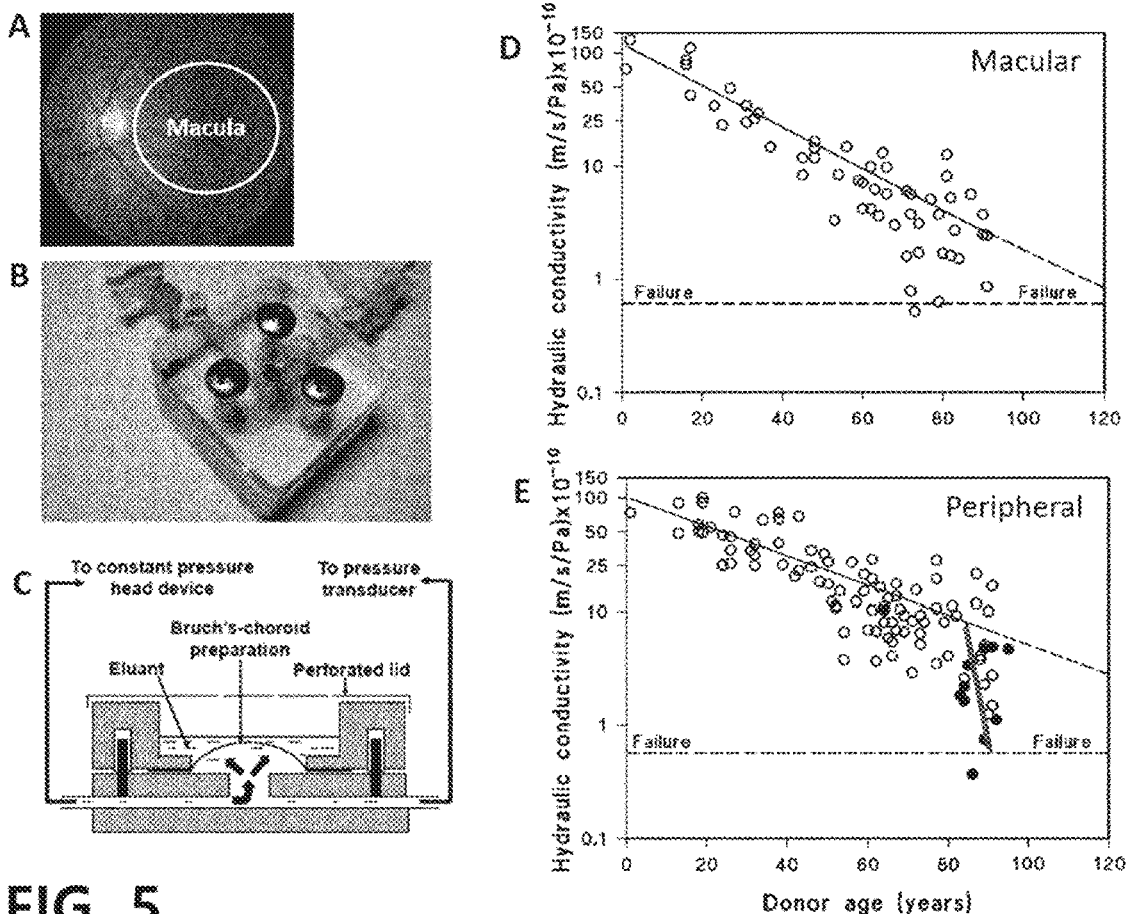
FIG. 5 illustrates changes in the hydraulic conductivity of a human Bruch's membrane due to aging of normal people and macular degeneration patients.

First, the hydraulic conductivity of the Bruch's membranes isolated from the donated eyes was measured to determine a waste transport ability. An isolated Bruch's membrane was loaded in an open-type Using chamber to measure changes in the quantity of fluid under hydrostatic pressure, and changes in hydraulic conductivity were calculated (see FIGS. 5B and 5C). As a result, the fluid transport capacity of the macular part decreased exponentially as aging progressed, and the transport capacity was reduced by half every 16 years (see FIG. 5D). The data in FIG. 5D shows the Y axis as a linear conversion of the exponential decay using a semi-log plot. To maintain the function of visual cells, the Bruch's membrane requires a minimum hydraulic conductivity function, which is indicated by a failure line. This function threshold value may be obtained by dividing the amount of fluid transported in the RPE by the hydrostatic pressure of the Bruch's membrane. The hydraulic conductivity of the Bruch's membrane needed to deliver the RPE fluid may be calculated from the following equation.

Hydraulic conductivity (HC)=flow of fluid/pressure

However, it is impossible to measure hydrostatic pressure across a human Bruch's membrane because of technical difficulties. In the case of monkeys, the pressure difference between the vitreous and choroidal space was estimated to be about 4 mmHg (534 Pa) (Emi et al., 1989) and is actually much lower. Using a value of 4 mmHg, the hydraulic conductivity required to transport the fluid (0.1248 ml/hour/mm$^2$) to the Bruch's membrane by the RPE may be calculated as $0.65 \times 10^{-10}$ m/sec/Pa.

When the transport function goes down, fluid accumulates below the RPE, causing RPE exfoliation and leading to the death of visual cells at the top. These symptoms occur in about 12-20% of patients with macular degeneration. In normal individuals, this line does not go down below the failure threshold for a lifetime, but it may cross the dysfunction threshold in a typical elderly population and serious problems such as abnormal night vision appear. In patients with macular degeneration, it is impossible to measure only the macular area independently because the macular area is severely damaged due to the nature of the disease. The hydraulic conductivity of the surrounding area also decreased exponentially in a similar pattern to that of the macula, and the half-life of the function was about 22 years (see FIG. 5E). The hydraulic conductivity measured in the peripheral part of 11 patients with macular degeneration may be confirmed to be below the mean regression line (see the black circles and red lines in FIG. 5E), and this demonstrates that a reduction in the material transport capability severely progressed in the peripheral area, not the macular area.

Figure 6:
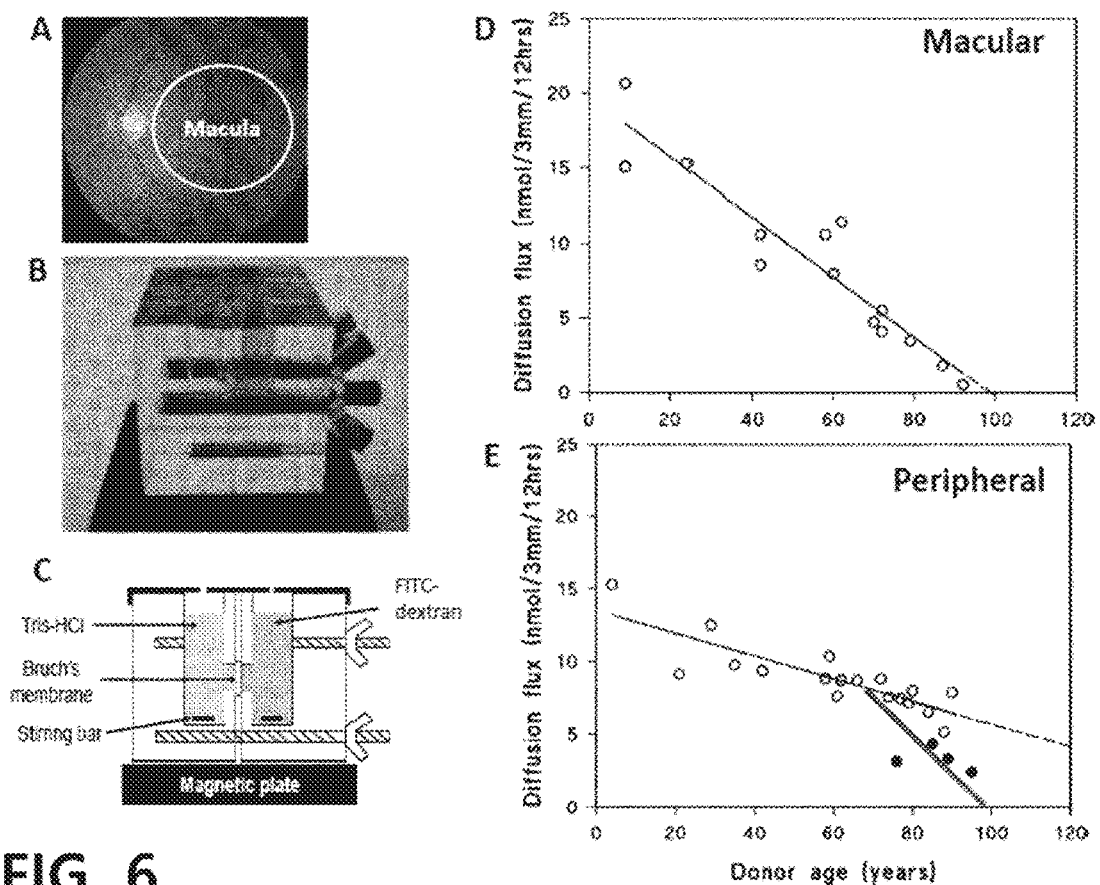
FIG. 6 illustrates changes in the degree of diffusion of a human Bruch's membrane due to aging of normal people and macular degeneration patients.

Next, a protein diffusion experiment was conducted to confirm the nutrient transport capacity of the Bruch's membrane. Specifically, the diffusion of FITC-dextran (MW 23 kDa) through the Bruch's membrane was examined using a common Using chamber (see FIGS. 6B and 6C). Dextran was chosen as a carrier material of similar size to most carrier proteins that play a role in the transport of substances such as vitamin A, trace metals, lipids, and the like. It was confirmed that the degree of diffusion of the protein-sized substance passing through the macular region was drastically decreased due to aging of the Bruch's membrane (see FIG. 6D). Despite the presence of normal levels of vitamins and antioxidants in the plasma, deficiencies in these substances are observed in the macular area. In the peripheral part, the degree of diffusion reduction was slower than in the macular area (see FIG. 6E), but in the case of patients with macular degeneration, it decreased sharply (see black circles and red lines of FIG. 6E). As such, if it is possible to measure the function of the macular area in patients with macular degeneration compared with the degree of reduction in the peripheral part, it can be verified that the degree is highly likely to be much faster and more rapid than in the peripheral area. This reduction in diffusion transport interferes with nutrient supply and removal of hazardous wastes, which in turn increases the risk of damage and death of the RPE and visual cells and causes blindness.

It is an object of the present invention to improve the transport capability of the Bruch's membrane in the general elderly and patients with macular degeneration. This is possible by removing waste products present in the membrane and reactivating the decomposition system in the membrane.

According to a clinical report, due to aging of the Bruch's membrane of the elderly, vitamin A is not sufficiently delivered from the blood to the RPE and visual cells, resulting in a lowered dark adaptation threshold. The ideal solution is to facilitate the transport capability of the Bruch's membrane and provide all the necessary nutrients present in the plasma for the Bruch's membrane. In the case of AMD patients, it is also necessary to improve the transport capacity of the Bruch's membrane so that the delivery of nutrients, antioxidants, metals, vitamins, and the like and the removal of toxic wastes are smoothly carried out in order to avoid metabolic damage which can cause illness.

Hereinafter, the present invention will be described in further detail with reference to the following examples. However, it will be obvious to those of ordinary skill in the art that these examples are provided for illustrative purposes only and are not intended to limit the scope of the present invention.

Example 1

Production of Red Ginseng Extract

Fresh ginseng was washed and steamed at 94° C. to 98° C., a steam pressure of 3 kg/cm$^2$, and a pressure of 1.5 kg/cm$^2$, followed by primary drying at 60° C. to 70° C. for 12-20 hours, and drying in sunlight until the moisture content became 15% to 18%, thereby completing the production of red ginseng.

To prepare a solvent extract of the red ginseng, generally, one selected from water, ethanol, and a mixture thereof may be used for extraction. For primary extraction, water was added in an amount that was about 5 times to about 10 times the weight of raw ginseng, followed by extraction at 80° C. to 85° C. for 12 hours, and for secondary extraction, water was added in an amount that was about 5 times to about 10 times the weight of raw ginseng, followed by extraction at 80° C. to 85° C. for 8 hours, tertiary extraction was performed at 80° C. to 85° C. for 8 hours after water was added in an amount that was about 5 times to about 10 times the weight of raw ginseng, and then quaternary extraction was performed at 80° C. to 85° C. for 8 hours after water was added in an amount that was about 5 times to about 10 times the weight of raw ginseng. Thereafter, the resulting extract was filtered to remove impurities, cooled until the temperature reached 10° C. to 15° C., purified by centrifugation, and was then subjected to vacuum concentration, thereby completing the production of a red ginseng extract used in the examples of the present invention.

Example 2

Production of Sea Cucumber Extract

A dried sea cucumber was ground using a grinder to prepare sea cucumber powder, and 70% ethanol was added thereto, followed by extraction for about 3-6 hours. The ethanol was removed in a vacuum to prepare a sea cucumber extract for use in the examples of the present invention.

Example 3

Effect of Red Ginseng and Sea Cucumber Extracts on Enhancing Hydraulic Conductivity of Bruch's Membrane According to Concentration To investigate the effect of red ginseng and sea cucumber extracts on enhancing the transport function of the Bruch's membrane, the Bruch's membranes isolated from the eyes of 4 individuals aged between 69 and 84 were measured and expressed as a dose-response curve for improvement in hydraulic conductivity.

Specifically, each Bruch's membrane was mounted in an open-type Using chamber and perfused with Tris-HCl buffer via tubes under hydrostatic pressure, and a solution having passed through each Bruch's membrane after a certain period of time was collected and measured for fluid transport. For experimental groups, each membrane was treated with 0% to 10% of the red ginseng extract or 0% to 10% of the sea cucumber extract, cultured for 24 hours, and then fluid transport thereof was measured.

Figure 7:
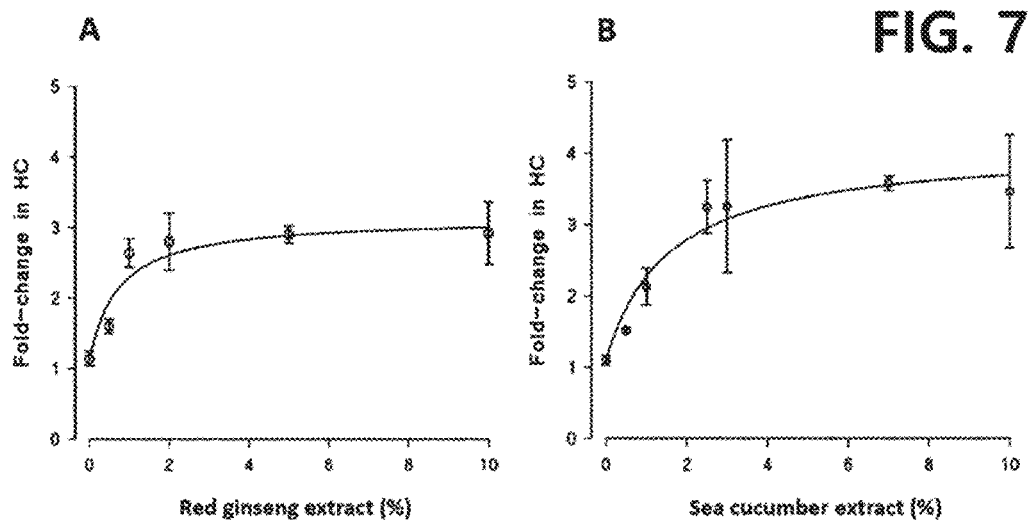
FIG. 7 illustrates results showing the effect of a red ginseng extract (A) and sea cucumber extract (B) of the present invention on enhancing a transport function of the Bruch's membrane.

Fold changes in responses according to the concentration of extract with respect to basal hydraulic conductivity measured before the response were expressed as graphs. As a result, as illustrated in FIG. 7, both the red ginseng and sea cucumber extracts exhibited hyperbolic dose-response curves, from which it was confirmed that the hydraulic conductivity of the membrane was enhanced as the dose increased. The experimental results showed that the red ginseng extract exhibited Km=0.7% and a 3.17-fold change in Vmax and the sea cucumber extract exhibited Km=1.56% and an improvement, i.e., a 4.11-fold change in Vmax. Thus, it was confirmed that each of the red ginseng and sea cucumber extracts was saturated, showing the maximum improvement in hydraulic conductivity at a concentration of about 3%.

It was confirmed that, in the saturated state, the red ginseng extract exhibited an about 3-fold increase in hydraulic conductivity and the sea cucumber extract exhibited an about 3.2-fold increase in hydraulic conductivity compared to when either extract was not added, from which it was confirmed that the red ginseng extract and the sea cucumber extract were able to have a significant effect on enhancing the transport function of the Bruch's membrane over various age groups.

Example 4

Effect of Repeated Treatment with Red Ginseng Extract on Enhancing

Hydraulic Conductivity of Bruch's Membrane

To examine whether the transport function of the Bruch's membrane was enhanced upon treatment with the red ginseng extract one or more times, an experiment for measuring hydraulic conductivity using Bruch's membranes isolated from the eyes of donors aged between 73 and 79 was carried out.

Specifically, the experiment was conducted in the same manner as in Example 3, except that only Tris-HCl was used for a control, and each experimental group was treated with a 2.5% red ginseng extract. The samples were subjected to primary culture to measure fluid transport, and further treated with a 2.5% red ginseng extract, followed by culture for 24 hours, followed by secondary measurement.

As a result of primary culture of the Bruch's membrane along with the 2.5% red ginseng extract, donors aged 73 exhibited an improvement in hydraulic conductivity from $0.91 \times 10^{-10}$ m/s/Pa to $1.94 \times 10^{-10}$ m/s/Pa and donors aged 79 exhibited an improvement in hydraulic conductivity from $1.36 \times 10^{-10}$ m/s/Pa to $3.38 \times 10^{-10}$ m/s/Pa. Upon treatment with the red ginseng extract twice, significant effects, i.e., increases in hydraulic conductivity from $1.94 \times 10^{-10}$ m/s/P to $2.68 \times 10^{-10}$ m/s/P ($p<0.05$) and from $3.38 \times 10^{-10}$ m/s/P to $5.07 \times 10^{-10}$ m/s/P ($p<0.005$) were exhibited in donors aged 73 and 79, respectively.

Figure 8:
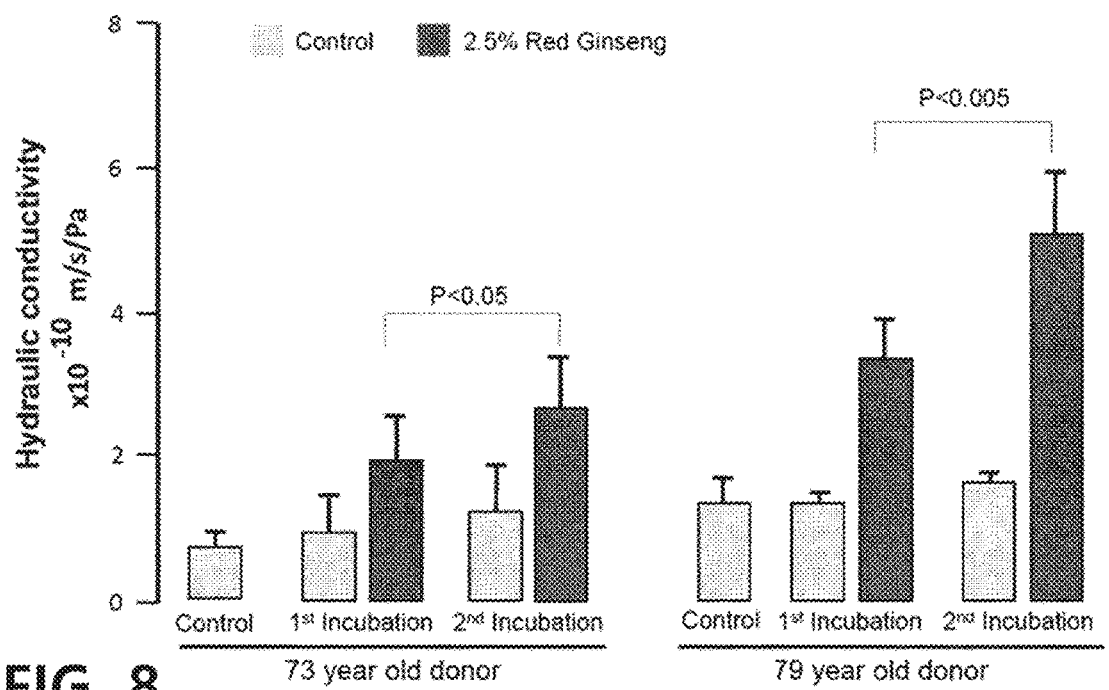
FIG. 8 illustrates results showing a hydraulic conductivity enhancement effect of the Bruch's membrane by repeated treatment with a red ginseng extract according to an embodiment of the present invention.

The results are illustrated in FIG. 8, from which it was confirmed that, while there is no change in the control even when exposed to the extract twice, the transport ability of the Bruch's membrane was further enhanced when repeatedly exposed to the red ginseng extract.

Example 5

Effect of Red Ginseng and Sea Cucumber Extracts on Enhancing Hydraulic Conductivity of Bruch's Membrane To confirm the effect of the red ginseng extract prepared according to Example 1, the sea cucumber extract prepared according to Example 2, and a mixture thereof on enhancing the hydraulic conductivity of the Bruch's membrane, an experiment was carried out in the same manner as in Example 3 using the Bruch's membranes of the eyes of donors aged between 12 and 89.

Figure 9:
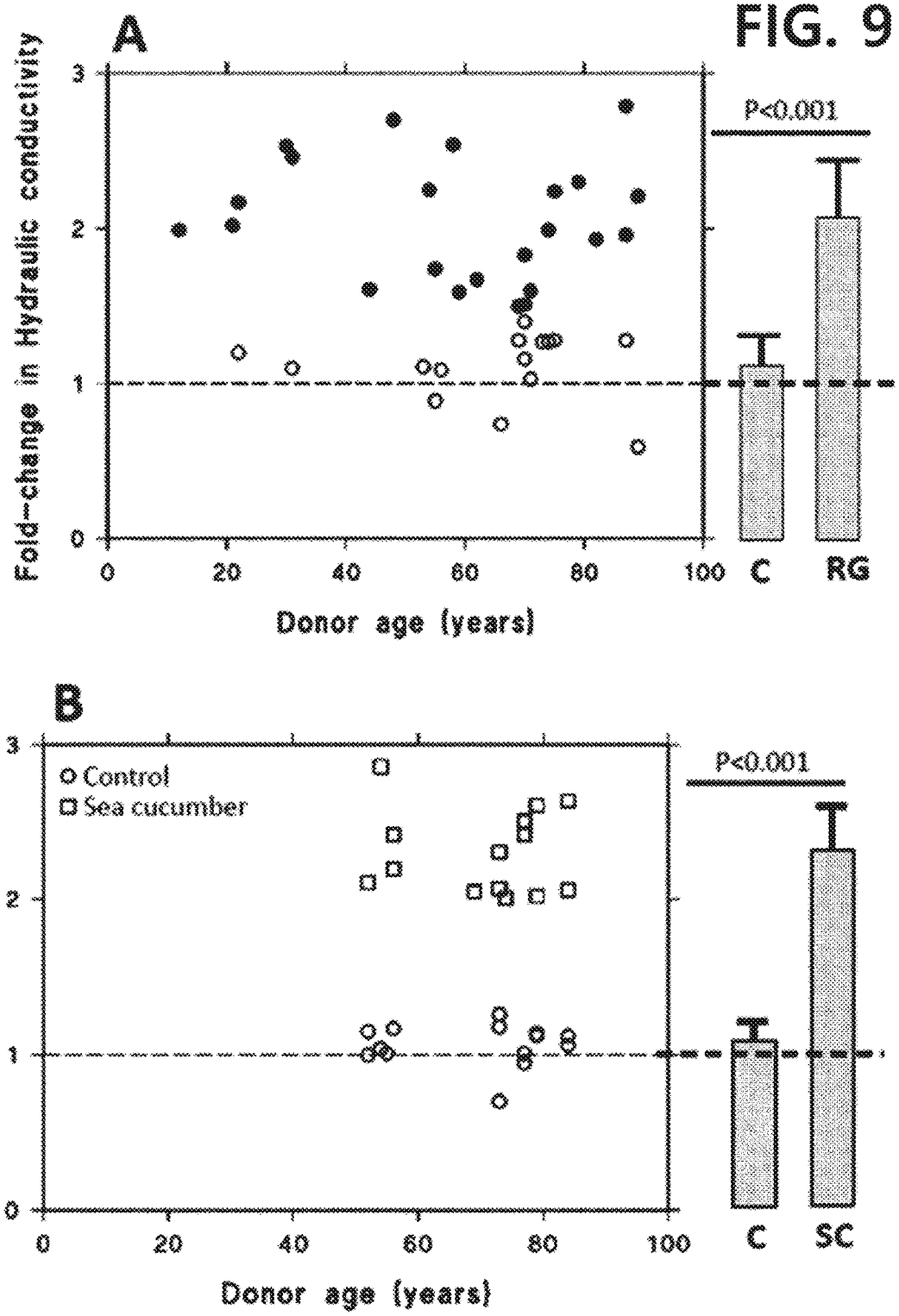
FIG. 9 illustrates results showing the effect of a red ginseng or sea cucumber extract of the present invention on enhancing the transport function of the Bruch's membrane.

Specifically, the Bruch's membranes isolated from the eyes of 38 donors (between 12 and 89 years old) were cultured together with 10% of the red ginseng extract for 24 hours, and Tris-HCl was used as a control. The results are illustrated in FIG. 9A, from which it was confirmed that a 2.2-fold increase in hydraulic conductivity of the Bruch's membrane was exhibited upon treatment with the red ginseng extract (control 1.11±0.22 (n=15, expressed by ○), group treated with 10% red ginseng extract 2.05±0.38 (n=23, expressed by •); units: $10^{-10}$ m/s/Pa, $p<0.001$).

Next, the Bruch's membranes isolated from the eyes of 28 donors (between 52 and 84 years old) were cultured together with 2.5% of the sea cucumber extract for 24 hours, and Tris-HCl was used as a control. The results are illustrated in FIG. 9B, from which it was confirmed that the sea cucumber extract increased the hydraulic conductivity of the Bruch's membrane 2.3-fold ($p<0.001$).

Figure 10:
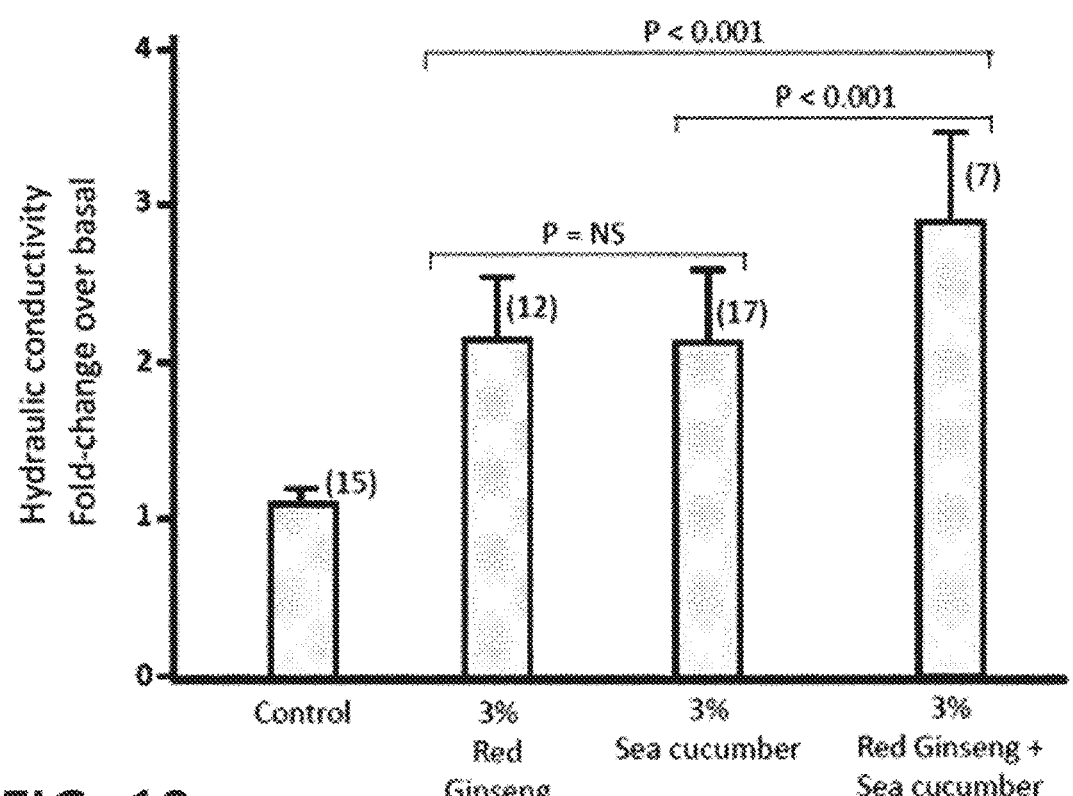
FIG. 10 illustrates a synergistic effect of a red ginseng and sea cucumber composite extract of the present invention on enhancing the transport function of the Bruch's membrane.

In addition, to confirm a synergistic effect upon co-treatment with the red ginseng extract and the sea cucumber extract, the Bruch's membranes isolated from the eyes of 17 donors (between 52 and 84 years old) were cultured for 24 hours along with Tris-HCl buffer (control), 3% of the red ginseng extract, 3% of the sea cucumber extract, or a mixture thereof, and the results are illustrated in FIG. 10.

As a result, the red ginseng extract and the sea cucumber extract similarly enhanced the hydraulic conductivity of the Bruch's membrane (red ginseng: 2.15±0.33-fold increase, sea cucumber: 2.13±0.47-fold increase, Mean±SD), and a composite of the two extracts exhibited a 2.89±0.58-fold increase in hydraulic conductivity. From these results, it was confirmed that an excellent improvement effect, which was statistically significant, was exhibited when treated with the composite extract compared to the single extract ($p<0.001$, Mean±SD).

Such an effect of the red ginseng and sea cucumber extracts on enhancing hydraulic conductivity is the same as a rejuvenation effect of making the Bruch's membrane appear to be about 20 to about 25 years old. Due to the hydraulic conductivity improvement effect, the failure threshold of the eyes is not crossed, whereby the risk for pathological progression such as macular degeneration may be reduced, or a reduction in vision due to aging may be prevented.

Example 6

Effect of Red Ginseng and Sea Cucumber Extracts on Removing Lipid Waste Products of Bruch's Membrane Cholesterol esters, cholesterol, triglycerides, and phospholipids are the major constituents of lipid waste products of the Bruch's membrane. Dose-response experiments were conducted to examine whether the red ginseng extract and the sea cucumber extract have an effect of removing lipid extracts accumulated in the Bruch's membrane.

Specifically, the Bruch's membranes isolated from the eyes of four donors (between 50 and 82 years old) were homogenized by mixing in Tris-HCl buffer, and the insoluble pellet containing the supernatant and lipid waste was separated by centrifugation. The separated pellet was mixed again with Tris-HCl buffer and incubated with the red ginseng extract or sea cucumber extract at a concentration of 0% to 2.5% in a 37° C. incubator for 24 hours. After the incubation, each sample was centrifuged and the amount of lipid secreted from the pellet into the supernatant was quantified by thin layer chromatography (TLC) on a silica gel plate.

Figure 11:
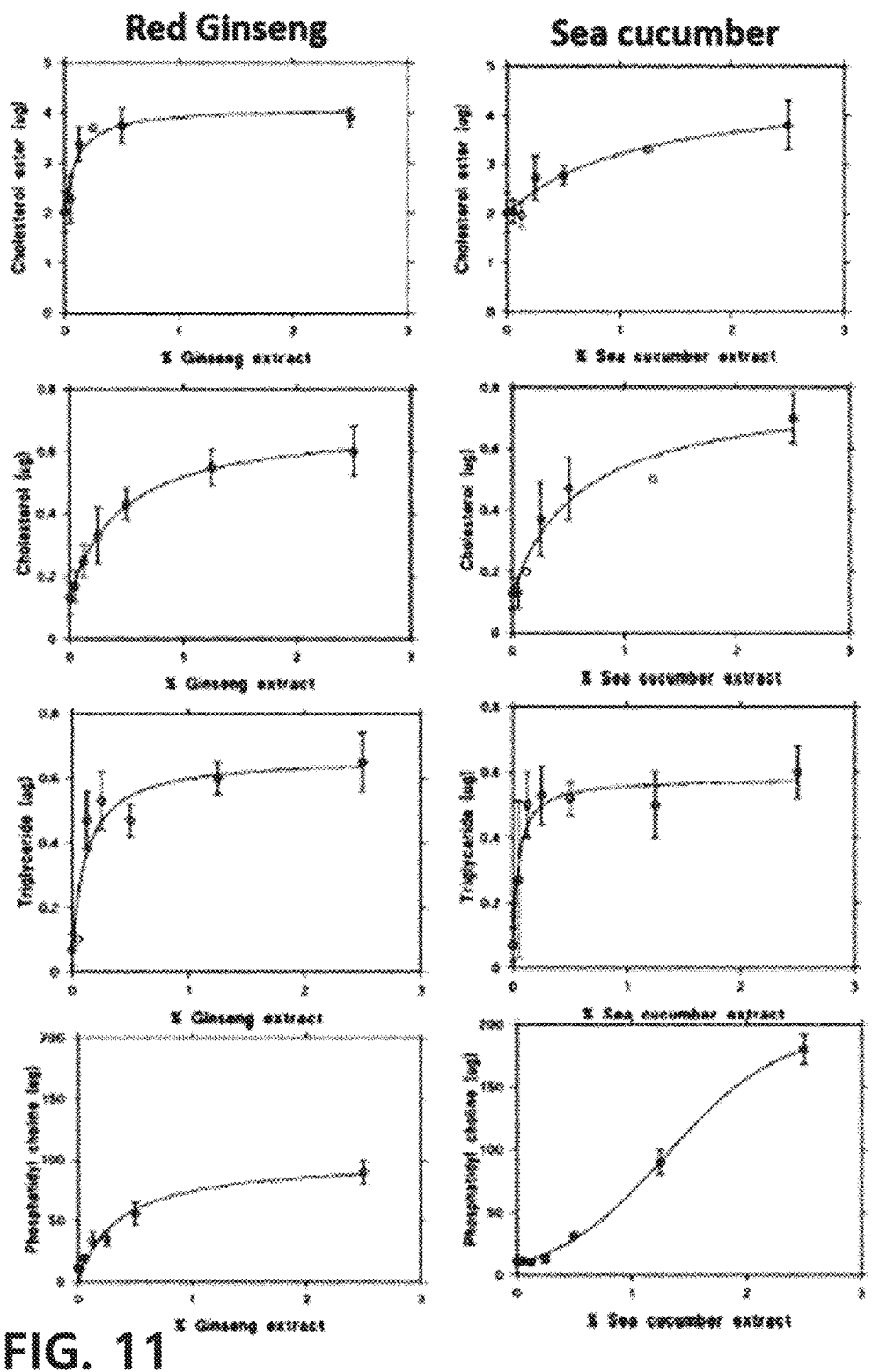
FIG. 11 illustrates dose-response curves showing the effect of a red ginseng extract and sea cucumber extract of the present invention on secreting lipids from the Bruch's membrane.

As a result, the dose-response curves, lipid secretion data, and kinetics of various types of lipid secretion are shown in FIGS. 11 and 12. As illustrated in FIG. 11, it was found that a cholesterol ester, cholesterol, a triglyceride, and a phospholipid, which had been deposited in the Bruch's membrane, when cultured together with the red ginseng and sea cucumber extracts, were secreted to remove various kinds of lipids from the membrane. Both extracts reached a saturation state with the maximum effect at a concentration of about 2.5%. In addition, as a result of comparing the lipid secretion data (see FIG. 12A) and the secretion effect (see FIG. 12B) of each extract, it was confirmed that, since the removal effects of the red ginseng extract and the sea cucumber extract are different according to the type of lipid, a composition consisting of the two extracts was the most effective in removing lipid wastes of the Bruch's membrane.

Example 7

Effect of Red Ginseng and Sea Cucumber Extracts on Secreting MMPs of Bruch's Membrane MMPs of the Bruch's membrane are present in a free form or in a form bound to the membrane. To confirm whether red ginseng and sea cucumber extracts are capable of removing the MMPs from the Bruch's membrane, first, MMPs bound to the membrane were investigated in the isolated Bruch's membrane.

The isolated Bruch's membrane was mounted in an open-type Using chamber and perfused with Tris-HCl buffer to remove materials in a free state. Real-time measurement was performed on fluid passing through the membrane, the amounts of MMPs secreted were confirmed by gelatin zymography, and after the experiment, a Bruch's membrane having a diameter of 6 mm was cut to measure MMP contents.

The free MMPs were removed within 1 hour after perfusion started, and then slowly secreted and almost all free MMPs were removed within 5 hours of perfusion (see FIG. 13). After free MMPs were secreted from the membrane, the Bruch's membrane was separated from the chamber, followed by extraction of MMPs remaining on the membrane using SDS buffer. It was confirmed that MMPs present in a soluble or free form were mostly secreted slowly between 5 and 12 hours of perfusion, but are not removed and remained on the membrane even after 5 to 12 hours of perfusion since most MMPs present in the Bruch's membrane are bound to or trapped in the membrane.

To examine whether the membrane-bound or trapped MMPs could be removed by the red ginseng and sea cucumber extracts, the Bruch's membranes isolated from the eyes of donors aged 73 and 79 were perfused with Tris-HCl for 12 hours to first secrete and remove free MMPs. Subsequently, each Bruch's membrane was perfused together with 2.5% of the red ginseng extract (RG), 2.5% of the sea cucumber extract (SC), and an extract mixture (RG+SC), and after 24 hours, perfused again with Tris-HCl buffer to confirm the amounts of secreted MMPs by gelatin zymography.

As a result, as illustrated in FIG. 14, it was confirmed that the MMPs having been bound to the membrane were secreted when treated with the red ginseng extract (RG), the sea cucumber extract (SC), and the composite extract of the red ginseng and sea cucumber extracts (RG+SC). Referring to FIG. 14, MMPs of control (C) were observed, from which it was confirmed that free MMPs could not be completely removed even after 12 hours of perfusion. Nevertheless, in the case of the Bruch's membrane using the 2.5% red ginseng extract (RG), it was confirmed that MMPs bound to the membrane, such as HMW1, and non-active and active forms of MMP2 and MMP9 were effectively secreted. The 2.5% sea cucumber extract (SC) had an MMP secretary effect similar to that of the red ginseng extract, and particularly had an excellent effect of removing a large amount of HMW2 bound to the membrane. The composite of the red ginseng and sea cucumber extracts (RG+SC) exhibited a stronger effect on removing MMPs bound to the membrane compared to the red ginseng or sea cucumber extract, from which a synergistic effect of the composite was confirmed.

As described above, the composite of the red ginseng and sea cucumber extracts is the most effective for the removal of MMPs trapped in the membrane, and a combination of these extracts acts on the secretion of a high molecular weight compound bound to or trapped in the membrane, thereby exhibiting an excellent effect on enhancing the transport capability of the Bruch's membrane. The most important thing is for the composite extract to be capable of normalizing a secretary system of the membrane through the removal of activated MMP2 and MMP9, which is effective in degrading abnormal proteins, thus helping regenerate the Bruch's membrane. In vivo, it is anticipated that, due to improved porosity of the Bruch's membrane, the composite extract is able to play an effective role in regenerating and degrading the Bruch's membrane together with new MMPs secreted by the RPE.

Example 8

Effect of Red Ginseng and Sea Cucumber Extracts on Secreting MMPs Present in Pellet of Bruch's Membrane of Human Eye To confirm the secretion effect of MMPs from the Bruch's membrane of red ginseng and sea cucumber extract, Bruch's membranes isolated from the two eyes of a 75-year-old donor were used. MMPs were present in the pellet of the Bruch's membrane used as a sample in a form of being trapped in or bound to the membrane. A certain volume of the pellet was cultured with Tris-HCl buffer as a control, and experimental groups were cultured with a 2.5% red ginseng extract or a 2.5% sea cucumber extract. After culture at 37° C. for 24 hours, centrifugation was performed to measure the amount of MMP secreted into the supernatant and MMPs present in a state bound to the pellet.

Figure 15:
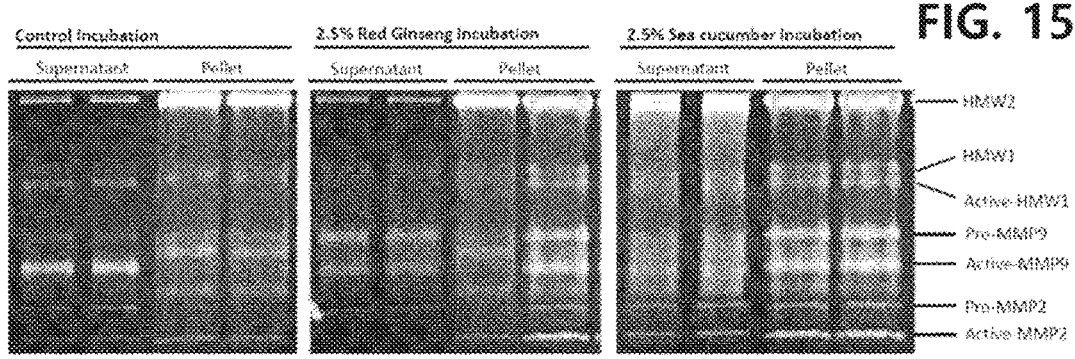
FIG. 15 illustrates results of confirming the secretion of different types of MMPs from waste products of the Bruch's membrane when a red ginseng extract and a sea cucumber extract of the present invention were used.

As a result, as illustrated in FIG. 15, activated MMP2 and MMP9 were secreted in small amounts in the control, and HMW2 remained bound to the pellet in most cases. Upon treatment with the red ginseng extract, a somewhat activated enzyme was secreted, but HMW2 still remained in the membrane like in the control. Meanwhile, it was confirmed that, upon treatment with the sea cucumber extract, most of the HMW2 was secreted and activated forms of HMW1, MMP2, and MMP9 were also secreted. From these results, it was confirmed that the sea cucumber extract secreted the activated form of HMW1 and precursor forms of pro-MMP2 and pro-MMP9 from the membrane to thereby remove waste products present in the Bruch's membrane, thus providing a positive effect on enhancing the transport function of the membrane.

The data confirmed in the above examples of the present invention clearly show that the red ginseng extract and the sea cucumber extract each exhibits an effect of enhancing the function of the Bruch's membrane, but have different action mechanisms in terms of an effect of secreting lipids and various types of MMPs present in the Bruch's membrane. Thus, it is evident that a composite of two types of extracts exhibits a synergistic effect compared to the case in which the two extracts are separately used, and it was confirmed from experimental results that the composite extract actually had a remarkably great effect on enhancing the structure and function of the Bruch's membrane.

The regeneration effect of the Bruch's membrane identified in the laboratory conditions will be further amplified in vivo by an additional action with the RPE. Therefore, these extracts provide the possibility of treating various diseases and visual impairment due to aging by raising the functional curve that declines by aging through improvement of the substance transporting ability of the Bruch's membrane. Since there are individual differences in the response to substances and the compositions of individual lipid waste products are different from each other, it is very ideal for overcoming heterogeneity by using a complex of ginseng/red ginseng and a sea cucumber.

Figure 16:
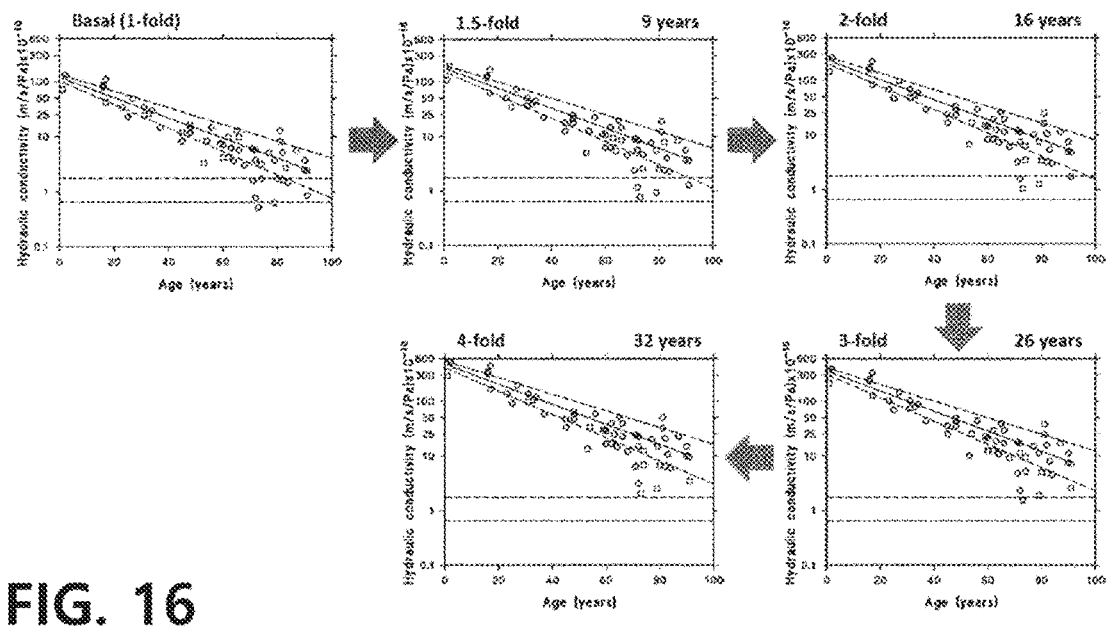
FIG. 16 illustrates results of confirming the effect of a composite extract of red ginseng and a sea cucumber of the present invention on delaying aging by adjusting the hydraulic conductivity curves upward.

Specifically, the treatment strategy proposed in the present invention improves the material transporting ability resulting from aging as shown in FIG. 16, thereby raising the straight line upward. A 1.5-fold improvement in hydraulic conductivity rejuvenates the function of the Bruch's membrane by 9 years and a 4-fold improvement in hydraulic conductivity improves the donor's eye function by 32 years. Thus, the degree of improvement may be determined according to the age group of the treatment target. In the general population that has not yet had visual illnesses, eye health may be maintained by taking low doses, and in the elderly population, higher doses may be used to prevent aging and Bruch's membrane hypofunction-related diseases due to aging. For patients with signs of eye disease due to aging, much higher doses may be used to delay or treat the progression of the disease.

Example 9

Effect of Ginseng and Sea Cucumber Extracts on Enhancing Hydraulic Conductivity of Bruch's Membrane To confirm the synergistic effect upon co-treatment with ginseng and sea cucumber extracts, Bruch's membranes isolated from pig eyes were cultured for 24 hours together with Tris-HCl buffer (control), 0.5% ginseng extract, 0.5% sea cucumber extract, a mixture of the ginseng and sea cucumber extracts, and the results are illustrated in Table 1 below and FIG. 17.

As a result, the ginseng extract and the sea cucumber extract improved the hydraulic conductivity of the Bruch's membrane (ginseng: 1.81±0.18-fold increase, sea cucumber: 2.32±0.05-fold increase, Mean±SD), and the composite of the two extracts increased the hydraulic conductivity 3.58±0.65 fold. From the results, it was confirmed that an excellent improvement effect, which was statistically significant, was exhibited when treated with the composite extract compared to the single extract ($p<0.05$, Mean±SD).

TABLE 1

|  | Mean | SD | n |
| --- | --- | --- | --- |
| Control | 1.36 | 0.26 | 11 |
| 0.5% White Ginseng | 1.81 | 0.18 | 3 |
| 0.5% SC | 2.32 | 0.05 | 4 |
| 0.5% White Ginseng + SC | 3.58 | 0.65 | 3 |

The invention claimed is:

1. A method of preventing, delaying, or treating a Bruch's membrane hypofunction-related disease by enhancing a transport function of the Bruch's membrane, the method comprising:
    administering, to a subject in need of such prevention, delaying or treatment, a composition comprising:
    a composite extract of ginseng and a sea cucumber,
    wherein the Bruch's membrane hypofunction-related disease is selected from the group consisting of age-related macular degeneration (AMD), Sorsby's fundus dystrophy, Malattia Levintanese (ML), Stargardt disease, Best's vitelliform retinal dystrophy, and Doyne's honeycomb retinal dystrophy (DHRD).

2. The method of claim 1, wherein the composite extract enhances the transport function by improving hydraulic conductivity or a material diffusion function of the Bruch's membrane.

3. The method of claim 1, wherein the composite extract enhances the transport function by removing a protein or lipid bound to or trapped in the Bruch's membrane.

4. The method of claim 1, wherein the composite extract regenerates the Bruch's membrane and enhances a function of the Bruch's membrane.

5. The method of claim 4, wherein the composite extract regenerates the Bruch's membrane by removing high molecular weight complexes 1 (HMW1), high molecular weight complexes 2 (HMW2), or a lipid component which are bound to or deposited on the Bruch's membrane, and enhances the function of the Bruch's membrane.

6. The method of claim 4, wherein the composite extract regenerates the Bruch's membrane by secreting, from a matrix of the Bruch's membrane, pro-matrix metalloproteinases 2 (pro-MMP2), pro-matrix metalloproteinases 9 (pro-MMP9), active matrix metalloproteinases 2 (MMP2), and active matrix metalloproteinases 9 (MMP9), and enhances the function of the Bruch's membrane.

7. The method of claim 4, wherein the composite extract regenerates the Bruch's membrane by activating a secretion of active MMPs from a retinal pigment epithelium (RPE), and enhances the function of the Bruch's membrane.

8. The method of claim 1, wherein the composition further comprising one or more components selected from the group consisting of amino acids, antioxidants, vitamins, minerals, metals, lutein, astaxanthin, zeaxanthin, and bilberry extracts.

9. The method of claim 1, wherein the ginseng is red ginseng.

10. The method of claim 1, wherein the ginseng is white ginseng.

* * * * *